(12) United States Patent
Alli et al.

(10) Patent No.: US 10,188,617 B2
(45) Date of Patent: Jan. 29, 2019

(54) MODULATION OF CELLULAR DNA REPAIR ACTIVITY TO INTERCEPT MALIGNANCY

(71) Applicant: THE BOARD OF TRUSTEES OF THE LELAND STANFORD JUNIOR UNIVERSITY, Stanford, CA (US)

(72) Inventors: Elizabeth Alli, Winston-Salem, NC (US); James M. Ford, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 20 days.

(21) Appl. No.: 14/774,623

(22) PCT Filed: Mar. 11, 2014

(86) PCT No.: PCT/US2014/023351
§ 371 (c)(1),
(2) Date: Sep. 10, 2015

(87) PCT Pub. No.: WO2014/164730
PCT Pub. Date: Oct. 9, 2014

(65) Prior Publication Data
US 2016/0038444 A1 Feb. 11, 2016

Related U.S. Application Data

(60) Provisional application No. 61/777,659, filed on Mar. 12, 2013.

(51) Int. Cl.
*A61K 31/16* (2006.01)
*A61K 31/165* (2006.01)
*A61K 31/18* (2006.01)
*A61K 31/64* (2006.01)
*C12Q 1/6886* (2018.01)
*G01N 21/64* (2006.01)

(52) U.S. Cl.
CPC ............ *A61K 31/18* (2013.01); *A61K 31/165* (2013.01); *A61K 31/64* (2013.01); *C12Q 1/6886* (2013.01); *G01N 21/6486* (2013.01); *C12Q 2600/156* (2013.01); *C12Q 2600/158* (2013.01); *Y02A 50/473* (2018.01)

(58) Field of Classification Search
CPC combination set(s) only.
See application file for complete search history.

(56) References Cited

U.S. PATENT DOCUMENTS

| 7,754,463 | B2 | 7/2010 | D'Andrea |
| 7,993,853 | B2 | 8/2011 | Scholl et al. |
| 2005/0196467 | A1 | 9/2005 | Giampapa |
| 2009/0076019 | A1 | 3/2009 | Tyers et al. |
| 2010/0048709 | A1 | 2/2010 | Wafa et al. |
| 2012/0207856 | A1 | 8/2012 | Goel et al. |

FOREIGN PATENT DOCUMENTS

| WO | 2007136857 A2 | 11/2007 |
| WO | 2008117314 A2 | 10/2008 |
| WO | 2011097269 A1 | 8/2011 |
| WO | 2011162416 A1 | 12/2011 |
| WO | 2012100248 A1 | 7/2012 |
| WO | 2012135831 A1 | 10/2012 |

OTHER PUBLICATIONS

Alli, Elizabeth, et al., "Therapeutic Targeting of BRCA1-Mutated Breast Cancers with Agents That Activate DNA Repair," Cancer Research (2014) 74(21):6205-6215.
Jung, Hwa Jin, et al., "Enhancement of Methyl Methanesulfonate-Induced Base Excision Repair in the Presence of Selenomethionine on p53-Dependent Pathway," Journal of Medicinal Food (2009) 12(2):340-344.
Katiyar, Santosh K., "Green tea prevents non-melanoma skin cancer by enhancing DNA repair," Archives of Biochemistry and Biophysics (2011) 508(2):152-158.
Madhusudan, Srinivasan, et al., "Isolation of a small molecule inhibitor of DNA base excision repair," Nucleic Acids Research (2005) 33(15):4711-4724.
Ramos, A., et al., "Dietary prevention of colon cancer phytochemical protection of DNA damage and induction of DNA repair in colonocytes," European Journal of Cancer, Supplement (2009) 7(2):106 (Abstract).
Alli, E., et al., "Defective Repair of Oxidative DNA Damage in Triple-Negative Breast Cancer Confers Sensitivity to Inhibitition of Poly (ADP-Ribose) Polymerase," Cancer Res (2009) 69(8):3589-3596.
Botto, X., et al., "Elevated levels of oxidative DNA damage in patients with coronary artery disease," Coronary Artery Disease (2002) 13:269-274.
Burley, J., "Structure and intermolecular interactions of glipizide from laboratory X-ray powder diffraction," Acta Crystallographica Section B (2005), B61:710-716.
Emanuel, P., et al., "A review of DNA repair and possible DNA-repair adjuvants and selected natural anti-oxidants," Dermatology Online Journal (2007) 13(3):10.
Engler, R., et al., Sulfonylurea KATP Blockade in Type II Diabetes and Preconditioning in Cardiovascular Disease, Circulation (1996) 94:2297-2301.

(Continued)

*Primary Examiner* — Samira J Jean-Louis
(74) *Attorney, Agent, or Firm* — Brian E. Davy; Bozicevic, Field & Francis LLP

(57) ABSTRACT

Disclosed herein are methods for identifying compounds that enhance base excision repair, as well as compounds identified thereby and methods of using such compounds in the interception of malignancy, i.e. the prevention of progression of a disease from a state of susceptibility to active disease. Exemplified compounds are acetohexamide and related compounds, as well as benserazide and analogs thereof. Exemplified malignancies are those of human breast cells carrying mutations, in particular, SUM149 cells and HCC1937 cells, which cells carry BRCA1 mutations.

15 Claims, 18 Drawing Sheets

(56) References Cited

OTHER PUBLICATIONS

Hartman, A., et al., "BRCA1 and p53: compensatory roles in DNA repair," J Mol Med (2003) 81:700-707.

Maksimenko, A., et al., "A molecular beacon assay for measuring base excision repair activities," Biochem Biophys Res Commun (2004) 319(1):240-246.

Mikusova, V., et al., "Mitoxantrone in Combination with a DNA-PK Inhibitor: in ISR Possible Therapy of Promyelocytic Leukaemia Resisant Forms," Folia Biologica (Praha) (2011) 57:200-205.

5A

5B

7A

7B

8A

8B

12A

12B

MODULATION OF CELLULAR DNA REPAIR ACTIVITY TO INTERCEPT MALIGNANCY

CROSS-REFERENCE TO RELATED APPLICATIONS

This application claims priority from U.S. Provisional Patent Application No. 61/777,659 filed on Mar. 12, 2013, which is hereby incorporated by reference in its entirety and is a U.S. national stage application of PCT/US2014/023351 filed on Mar. 11, 2014, which is also incorporated herein by reference in its entirety.

STATEMENT OF GOVERNMENTAL SUPPORT

This invention was made with Government support under contract NS061674 awarded by the National Institutes of Health. The Government has certain rights in this invention.

REFERENCE TO SEQUENCE LISTING, COMPUTER PROGRAM, OR COMPACT DISK

None.

BACKGROUND OF THE INVENTION

Field of the Invention

The present invention relates to the field of cancer prevention by use of agents that have been found to have the ability to intercept cancerous or pre-cancerous cells by activating or enhancing DNA repair activity of altered or damaged DNA.

Related Art

Presented below is background information on certain aspects of the present invention as they may relate to technical features referred to in the detailed description, but are not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Oxidative DNA damage (ODD) constitutes the majority of DNA damage in human cells due to reactive oxygen species (ROS), which are genotoxic agents generated endogenously by metabolism and other biological processes. ODD typically occurs as single-base alterations (i.e. lesions) and undergoes repair via the base excision DNA repair (BER) pathway. When left unrepaired, ODD results in mutagenesis. For example, the most common ODD lesion, 8-oxoguanine (8-OG), can mispair and result in GC→TA transversions. Alternatively, ODD converts to single- or double-stranded breaks and results in genomic instability. Overall, these events contribute to the initiation, progression, and maintenance of various malignancies, including breast cancer. However, little is known about the regulation of ODD.

To reduce the risk of developing cancer, chemopreventative drugs may be used by high-risk patients. Two such drugs, tamoxifen and raloxifene (Evista), are currently used in the prevention of invasive breast cancer. Both of these drugs belong to a class known as selective estrogen receptor modulators (SERMs), which block the effects of estrogen in the breast and other tissues. Toremifene, another SERM class drug, is used in advanced metastatic breast cancer. None of these drugs, however, are known to upregulate a cellular DNA repair mechanism.

SPECIFIC PATENTS AND PUBLICATIONS

Alli et al., "Defective Repair of Oxidative DNA Damage in Triple-Negative Breast Cancer confers Sensitivity to Inhibition of Poly(ADP-Ribose) Polymerase" Cancer Res 2009; 69: (8) Apr. 15, 2009 discloses an assay which is a cell-based DNA repair assay that consists of three basic steps: (a) oxidatively damaging a GFP-reporter gene; (b) adenoviral-mediated gene transfer for delivery of the damaged GFP-reporter gene into living cells; and (c) host-cell activation, which allows for repair of the oxidatively damaged reporter gene and expression of GFP. If the host cell repairs the gene, using base excision repair, a fluorescent signal will result from expression of the GFP.

Maksimenko et al., "A molecular beacon assay for measuring base excision repair activities," BBRC 319:240-246 (2004), discloses an assay of DNA excision repair that uses cell free extracts and cultured cells.

Emanuel et al., "A review of DNA repair and possible DNA-repair adjuvants and selected natural anti-oxidants," Dermatology Online Journal 13(3):10 (2007), suggests that certain compounds and proteins may have effects in increasing DNA repair, although breast cancer and BER are not mentioned.

U.S. Pat. No. 7,754,463, entitled "Inhibitors of USP1 Deubiquitinating Enzyme complex," relates to compositions and methods for inhibition of USP1, a deubiquitinase whose inhibition increases the resistance of eukaryotic cells to the damaging effects of ionizing radiation and DNA-damaging chemicals.

Hartman and Ford, "BRCA1 and p53: compensatory roles in DNA repair," J Mol Med 81:700-707 (2003), suggests that BRCA1 plays a role in several DNA repair pathways, including nucleotide excision repair (NER). It is suggested that BRCA1 affects DNA repair through transcriptional regulation of DNA recognition genes.

BRIEF SUMMARY OF THE INVENTION

The following brief summary is not intended to include all features and aspects of the present invention, nor does it imply that the invention must include all features and aspects discussed in this summary.

The present invention in general comprises a method of intercepting (or preventing) a progression from a pre-malignant condition to malignancy, such as may exist in (1) a subject having a known genetic mutation causing a predisposition to a certain type of cancer, (2) a subject having a measured level of cellular DNA repair activity that is below a normal level or (3) a subject having a family history that shows a statistically significant increase of likelihood of developing the malignancy.

The predisposition may include a pre-cancer, such as ductal carcinoma in situ, which is more benign than a cancerous tumor in that it does not have the ability to invade other parts of the body. The predisposition may be simply a genetic mutation, without any evidence of disease. The methods of the present invention comprise a method of administration of certain compounds to such subjects, where, as stated, the subjects do not at the time of administration have an active malignancy, but are at risk, due, for example, to a mutation in BRCA1 or BRCA2 (BReast CAncer genes 1 or 2). These compounds are those found to be active in an assay of DNA repair, but were not previously known to enhance such DNA base repair. These include the 94 compounds listed in Table 1 below.

In some embodiments, the present invention comprises the administration of agents that enhance DNA repair pathways in cells to persons who have been first identified as being at risk for malignancies that can develop when that person's inherited or acquired genomic characteristics make them susceptible to developing the malignancy. As an example, a person is administered such agents if he or she has a family history putting them at significant risk for developing such malignancy. This is described further below. As another example, one may select a candidate subject to be administered the present preventive therapy on the basis of a personalized estimate of breast cancer risk as described, e.g. in Gail, "Personalized estimates of breast cancer risk in clinical practice and public health," Stat Med. 2011 May 10; 30(10): 1090-1104.

In some embodiments, the malignancy is from the group comprising breast cancer, ovarian cancer, colon cancer, other forms of cancer, and various degenerative or sclerotic diseases, including but not limited to Alzheimer's disease, Parkinson's disease, amyotrophic lateral sclerosis, atherosclerosis, ischemic neuronal injuries, TMJ degenerative disease, cataracts, macular degeneration, retinal degeneration, rheumatoid arthritis, multiple sclerosis, or muscular dystrophy.

The identified mutations making a subject more susceptible to developing the malignancy may be mutations of BRCA1, mutations of BRCA2, mutations in p16, Rb or other mutations in oncogenes, such as CHEK2 and TP53 genes associated with Li-Fraumeni syndrome.

In some aspects of the present invention, a subject having a pre-malignant condition (e.g. a BRCA1 mutation, defective DNA repair, etc.) is treated with a compound that is a DNA repair agent that has already been approved for use in humans for other conditions, and is well tolerated and non-toxic. In certain embodiments, the DNA repair agent may be a sulfonylurea derivative. The sulfonylurea derivative may be selected from acetohexamide, glipizide, or analogs thereof. In other embodiments, the DNA repair agent is benserazide or analogs thereof. In some embodiments, a plurality of the DNA repair agents is administered to the subject in combination.

In some embodiments of the present invention, the genetic mutation is a heritable mutation, and may be selected from mutations in BRCA1, BRCA2, CHEK2, or XRCC2 genes. Other gene mutations use in the present methods are those in TP53 (tumor protein p53) and those which cause HNPCC (hereditary nonpolyposis colorectal cancer.)

Thus, the present invention comprises A method of preventing malignancy in a subject having a genetic predisposition to such malignancy, comprising the step of administering to said subject an effective amount of a DNA repair agent which is a compound selected from the group consisting of bepridilhydrochloride agmatinesulfate, ancitabinehydrochloride, 6-aminohexanoic acid, cytosine-1-beta-D-arabinofuranosidehydrochloride, ouabain, 5-bromo-2'-deoxyuridine. quinacrinedihydrochloride, cyclosporinA, diphenyleneiodoniumchloride, cantharidin, chelerythrinechloride, bretylium tosylate, CGP-74514A hydrochloride, 4-(2-aminoethyl)benzenesulfonyl fluoride hydrochloride, cantharidic acid, benserazidehydrochloride, SU6656, mitoxantrone, SU5416, (+)-brompheniraminemaleate 5-azacytidine, acetohexamide, benazolineoxalate, cyproteroneacetate, ebselen, calcimycin, 1-(4-chlorobenzyl)-5-methoxy-2-methylindole-3-aceticacid, clotrimazole, SB200646 hydrochloride, captopril, buspironehydrochloride, DL-p-chlorophenylalanine methyl ester hydrochloride, 8-(p-Sulfophenyl)theophylline, centrophenoxinehydrochloride, clonidinehydro chloride, 1-allyl-3,7-dimethyl-8-p-sulfophenylxanthine, O-(carboxymethyl)hydroxylamine hemihydrochloride, CGS-15943, 4-chloromercuribenzoicacid, phenylephrinehydrochloride, iodoacetamide, etoposide, diltiazemhydrochloride, CB34, SKF96365, actinonin, CP55940, beta-chloro-L-alaninehydrochloride, 9-amino-1, 2,3,4-tetrahydroacridinehydrochloride, pyrocatechol, OXA-22 iodide, dihydroergocristine methanesulfonate, agroclavine, GABA, GBR-12935dihydrochloride, SKF97541hydrochloride, gabaculinehydrochloride, dihydroouabain, AIDA, 2,3-butanedionemonoxime, L-asparticacid, sodium taurocholate, 5alpha-androstane-3alpha, 17beta-diol, indirubin-3'-oxime, danazol, reserpine, 2-methoxyestradiol, SB222200, 5-(N-methyl-N-isobutyl)amiloride, dipyridamole, PNU-37887A, A-315456, glipizide, 4-amino-1,8-naphthalimide S-(p-Azidophenacyl)glutathione, emetine dihydrochloride hydrate, 1-amino-1-cyclohexanecarboxylicacidhydrochloride, Z-L-phechloromethylketone, alpha-guanidinoglutaricacid, Bay11-7085, (+)-N-Allylnormetazocine hydrochloride, brefeldinA from Penicillium brefeldianum, carbetapentane citrate, colchicine, H-9 dihydrochloride, idarubicin, dequalinium analog, C-14 linker, amsacrinehydrochloride, 2,6-Diamino-4-pyrimidinone, gamma-acetylinic GABA, GW5074, ATPA, and rac-2-Ethoxy-3-hexadecanamido-1-propylphosphocholine.

The inventive methods may include use (on the appropriate subject as described herein) of bepridil hydrochloride, ancitabine hydrochloride, cytosine-1-beta-D-arabinofuranoside hydrochloride, 5-bromo-2'-deoxyuridine, cyclosporin A, cantharidin, bretylium tosylate, 4-(2-aminoethyl)benzenesulfonyl fluoride hydrochloride, glipizide, benserazide hydrochloride, mitoxantrone, (+)-brompheniramine maleate, acetohexamide, cyproterone acetate, calcimycin, clotrimazole, captopril, L-p-chlorophenylalanine methyl ester hydrochloride, and centrophenoxine hydrochloride.

In certain aspects the present invention comprises, in combination with the other aspects, a method wherein said malignancy is cancer. In certain aspects the present invention comprises, in combination with the other aspects, said predisposition to malignancy is associated with a mutation in a gene selected from the group consisting of BRCA1, BRCA2, CHEK2, XRCC2, TP53, and HPNCC. In certain aspects the present invention comprises, in combination with the other aspects, a method comprising a step wherein a DNA repair assay is conducted on a cell from the subject.

In certain aspects the present invention comprises, in combination with the other aspects, a method wherein the compound is benserazide including salts thereof. In certain aspects the present invention comprises, in combination with the other aspects, a method wherein the compound is an analogue of benserazide.

In certain aspects the present invention comprises, in combination with the other aspects, a method wherein the agent has the structural formula:

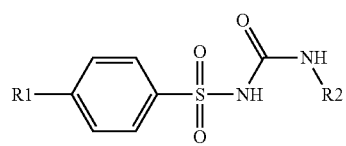

wherein:

R1 is selected from hydrogen, alkyl (C1 to C20), acetyl; and

R2 is selected from alkyl (C1 to C20) and cyclohexane.

In certain aspects the present invention comprises, in combination with the other aspects, a method wherein the agent is one of acetohexamide or glipizide.

In certain aspects the present invention comprises, in combination with the other aspects, a method wherein further comprising the step of testing said subject for the presence of a genetic mutation by determining a genotype of a normal somatic cell from said subject.

In certain aspects the present invention comprises, in combination with the other aspects, a method wherein comprising the step of testing a somatic cell from said subject for a level of base excision repair activity. In certain aspects the present invention comprises, in combination with the other aspects, a method wherein said testing comprises transfecting the somatic cell with an oxidatively damaged vector that is expressed only after repair of oxidative damage by the cell.

In certain aspects the present invention comprises, in combination with the other aspects, a method of preventing malignancy in a subject having a predisposition to such malignancy, comprising the steps of: (a) evaluating said subject for said predisposition by a base excision repair assay; and (b) administering to said subject an effective amount of an agent that has activity in a DNA repair assay if evaluating shows less than normal base excision repair activity.

In certain aspects the present invention comprises, in combination with the other aspects, a method wherein said agent is selected from one or more compounds listed in Table 1.

In certain aspects the present invention comprises, in combination with the other aspects, a method wherein evaluating a subject for the predisposition for a malignancy comprises testing for a genetic mutation in a cancer-associated gene. This may also comprise taking a family history from the subject. This may also comprise evaluating comprises measuring a level of oxidative DNA damage in a cell from said subject.

In certain aspects the present invention comprises, in combination with the other aspects, a method as the preceding wherein the compound is acetohexamide or benzaserazide.

The present methods in combination with the above, may also comprise evaluating the subject for a mutation in a gene selected from OGG1, APE1, BARD, BRCA1, BRCA2, CHEK1, CHK1, CHEK2, CHK2, FEN1, FPG, NIEL1, NIEL2, MYH, NTH1, NUDT1, MUTYH, PTEN, PARP1, TP53, TG, UNG, XRCC, XRCC2, XRCC3, and XRCC4

In certain aspects the present invention comprises, in combination with the other aspects, a method of preventing malignancy in a subject having a predisposition to such malignancy, comprising the step of administering to said subject an effective amount of a DNA repair agent as listed above. The predisposition to malignancy may be associated with a mutation in a gene selected from the group consisting of BRCA1, BRCA2, CHEK2, XRCC2, and TP53.

In certain aspects the present invention comprises, in combination with the other aspects, a method wherein the malignancy is breast cancer or HNPCC.

BRIEF DESCRIPTION OF THE DRAWINGS

FIG. 2A is an image of a well plate showing BrdU in a preliminary screen. FIG. 2B is a line graph showing Green Fluorescent Protein (GFP) signal detection by imaging. FIG. 2C is a line graph showing GFP signal detection by plate reading.

FIG. 4A is an image of a well plate showing positive and negative signals. FIG. 4B shows the results of GFP expression, which was calculated as % GFP-positive cells (GFP-positive cells/Hoechst 33342-positive cells×100) to determine CV, S/B, and Z'-factor. Coefficient of variability (CV), signal-to-background (S/B), and Z'-factor (and spatial uniformity) are all known calculations used to determine whether an assay is acceptable for HT-screening.

FIG. 4C reveals the number of GFP-positive cells for each positive control well (i.e. max signal; gray) and negative control well (i.e. min signal; black) arranged by row, then column (top) or by column, then row (bottom). No drift or edge effects were observed as evidenced by the lack of a significant trend in signal from left-to-right and top-to-bottom. Percent drift was calculated from the max signal (FIG. 4D).

In FIG. 5B, summed priority scores ranged from 1-10. For each summed priority score, the number of active compounds with and without potential cytotoxicity is shown (FIG. 5B). Compounds with a summed priority score of 1 (solid white bar in 5B) were eliminated and the remaining compounds were then defined as hits. A higher "summed priority score" predicts more robust BER activity. The gray portion of the bars in 5B indicates active compounds with potential cytotoxicity, and the black portion of the bars indicates active compounds without potential cytotoxicity.

DETAILED DESCRIPTION OF THE PREFERRED EMBODIMENT

Definitions

Figure 1:
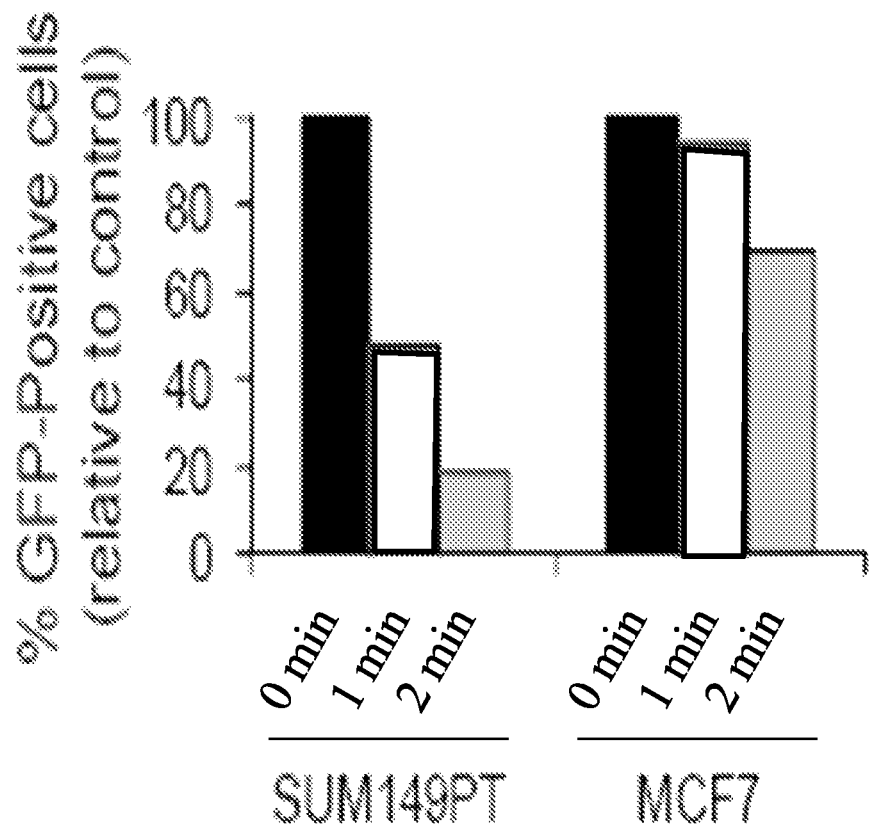
FIG. 1 is a bar graph showing deficient DNA repair activity of the SUM149PT cell line as compared to the MCF7 control cell line.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "derivative" as used herein, and conventionally, refers to a compound derived from another compound through one or more chemical transformations.

The term "DNA repair agent" as used herein refers to small molecules that activate or enhance base excision repair activity of oxidative DNA damage. Unlike antioxidants, which indirectly inhibit DNA damage, DNA repair agent may either stimulate repair by inhibiting an inhibitor of base excision repair, activate an activating event, e.g. DNA repair agents may promote protein-protein interactions, or repair damage by a yet undetermined mechanism.

The term "intercepting" as used herein refers to preventing a premalignant cell from progressing to cancer or, alternatively, obstructing an already malignant cell from further progression or delaying the onset of malignancy.

The term "alkyl" as used herein refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{20}$ for straight chains, $C_3$-$C_{30}$ for branched chains), and more specifically 20 or fewer carbon atoms. Likewise, some cycloalkyls have from 3-10 carbon atoms in their ring structure, and more specifically have 5, 6 or 7 carbons in the ring structure.

Moreover, the term "alkyl" (or "lower alkyl") as used herein is intended to include both "unsubstituted alkyls" and "substituted alkyls", the latter of which refers to alkyl moieties having substituents replacing a hydrogen on one or more carbons of the hydrocarbon backbone. Such substituents can include, for example, a halo, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "HNPCC" refers to hereditary nonpolyposis colorectal cancer, which is caused by mutation of the MSH2, MLH1, PMS2, MSH6, TGFBR2, or MLH3 gene. HNPCC is also known as Lynch syndrome, or Cancer Family Syndrome. The majority of HNPCC is caused by mutations in one of several mismatch-repair genes: MSH2, MSH6, and PMS1 on chromosome 2, MLH1 on chromosome 3, MSH3 on chromosome 5, and PMS2 on chromosome 7. MSH2 and MLH1 account for the majority of mutations in HNPCC families.

The term "effective amount" means the dosage (dose or amount, and frequency) of the agent referred to which, directly or indirectly, prevents or minimizes to a statistically significant degree the occurrence of the malignancy referred to over the course of preventive treatment with the agent.

As used herein, the term "malignancy" refers to a non-benign tumor or a cancer. As used herein, the term "cancer" connotes a type of proliferative disease which includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, haematological cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Overview

Described herein are methods and compositions related to intercepting or preventing malignancies associated with genetic mutations that create susceptibility to malignancies caused by DNA damage. Novel agents have been identified that may be used in subjects with deficient DNA repair mechanisms or pre-existing damaged DNA. These DNA repair agents may be administered to a patient at risk for a malignancy (e.g. breast cancer) associated with deficient DNA repair or prior to or during the onset of symptoms caused by such a malignancy. For example, a patient's cell may be used in the DNA repair assay as described herein to determine if the patient was a candidate for interception of a DNA repair agent. There are many different types of DNA repair including, but not limited to, base excision repair (BER), nucleotide excision repair (NER), mismatch repair, and double-strand break repair. The damage caused by deficient DNA repair may be described in several ways: BER-related damage, oxidative damage, or damage as a result of oxidative stress. As provided in further detail below, DNA damage was induced using a method that delivers oxidative stress, which is typically repaired by BER, but can be converted to single- or double strand breaks and repaired by other mechanisms.

Base excision repair is a mechanism by which an altered or damaged base is excised and replaced by a new, non-damaged base. Such damage may occur via chemical modification to a conventional purine or pyrimidine nucleobase. Such chemical modification may include: incorporation of uracil into DNA, deamination, alkylation, or oxidation of the bases. In certain embodiments, the DNA repair agents described herein effectively activate or enhance base excision repair enzymatic activity in order to reduce the occurrence of oxidative DNA damage.

DNA Repair Agents

In order to identify DNA repair agents that effectively enhanced base excision repair activity, potential candidate compounds from a chemical library were put through a high-throughput (HT) screening process based on a DNA repair assay as described in further detail below. The HT assay runs on the same principle as disclosed in Alli et al. Cancer Res 2009, but was modified for HT use, e.g. the amount of oxidative damage in the GFP reporter was greater in the HT assay. 94 potential compounds were identified. Table 1 lists these compounds:

TABLE 1

94 Potential Compounds for Enhancing BER

1. Bepridil hydrochloride
2. Ancitabine hydrochloride
3. Cytosine-1-beta-D-arabinofuranoside hydrochloride
4. 5-Bromo-2'-deoxyuridine
5. Cyclosporin A
6. Cantharidin
7. Bretylium tosylate
8. 4-(2-Aminoethyl)benzenesulfonyl fluoride hydrochloride
9. Benserazide hydrochloride
10. Mitoxantrone
11. (+)-Brompheniramine maleate
12. Acetohexamide

TABLE 1-continued

94 Potential Compounds for Enhancing BER

13. Cyproterone acetate
14. Calcimycin
15. Clotrimazole
16. Captopril
17. DL-p-Chlorophenylalanine methyl ester hydrochloride
18. Centrophenoxine hydrochloride
19. 1-Allyl-3,7-dimethyl-8-p-sulfophenylxanthine
20. CGS-15943
21. Phenylephrine hydrochloride
22. Etoposide
23. CB34
24. Actinonin
25. beta-Chloro-L-alanine hydrochloride
26. Pyrocatechol
27. Dihydroergocristine methanesulfonate
28. GABA
29. SKF 97541 hydrochloride
30. Dihydroouabain
31. 2,3-Butanedione monoxime
32. Sodium Taurocholate
33. Indirubin-3'-oxime
34. Reserpine
35. SB 222200
36. Dipyridamole
37. A-315456
38. 4-Amino-1,8-naphthalimide
39. Emetine dihydrochloride hydrate
40. Z-L-Phe chloromethyl ketone
41. Bay 11-7085
42. Brefeldin A from Penicillium brefeldianum
43. Colchicine
44. Idarubicin
45. Amsacrine hydrochloride
46. gamma-Acetylinic GABA
47. ATPA
48. Agmatine sulfate
49. 6-Aminohexanoic acid
50. Ouabain
51. Quinacrine dihydrochloride
52. Diphenyleneiodonium chloride
53. Chelerythrine chloride
54. CGP-74514A hydrochloride
55. Cantharidic Acid
56. SU 6656
57. SU 5416
58. 5-azacytidine
59. Benazoline oxalate
60. Ebselen
61. 1-(4-Chlorobenzyl)-5-methoxy-2-methylindole-3-acetic acid
62. SB 200646 hydrochloride
63. Buspirone hydrochloride
64. 8-(p-Sulfophenyl)theophylline
65. Clonidine hydrochloride
66. O-(Carboxymethyl)hydroxylaminehemihydrochloride
67. 4-Chloromercuribenzoic acid
68. Iodoacetamide
69. Diltiazem hydrochloride
70. SKF 96365
71. CP55940
72. 9-Amino-1,2,3,4-tetrahydroacridine hydrochloride
73. OXA-22 iodide
74. Agroclavine
75. GBR-12935 dihydrochloride
76. Gabaculine hydrochloride
77. AIDA
78. L-Aspartic acid
79. 5alpha-Androstane-3alpha,17beta-diol
80. Danazol
81. 2-methoxyestradiol
82. 5-(N-Methyl-N-isobutyl)amiloride
83. PNU-37887A
84. Glipizide
85. S-(p-Azidophenacyl)glutathione
86. 1-Amino-1-cyclohexanecarboxylic acid hydrochloride
87. alpha-Guanidinoglutaric acid
88. (+)-N-Allylnormetazocine hydrochloride
89. Carbetapentane citrate
90. H-9 dihydrochloride
91. Dequalinium analog, C-14 linker
92. 2,6-Diamino-4-pyrimidinone
93. GW5074
94. rac-2-Ethoxy-3-hexadecanamido-1-propylphosphocholine Exemplary data for top scoring compounds is given in Table 2 below:

TABLE 2

Exemplary data for top scoring compounds

| Priority score | compound | M.W. | EC50 (image analysis) | % BER (High) (image analysis) |
|---|---|---|---|---|
| 10 | Bepridil hydrochloride | 403 | 22.73 | 21.4 |
| 10 | Ancitabine hydrochloride | 262 | 19.82 | 25.5 |
| 10 | Cytosine-1-beta-D-arabinofuranoside hydrochloride | 280 | 22.78 | 18.3 |
| 10 | 5-Bromo-2'-deoxyuridine | 307 | 7.27 | 91.5 |
| 10 | Cyclosporin A | 1203 | 10.22 | 72.1 |
| 10 | Cantharidin | 196 | | 21.06 |
| 7 | Bretylium tosylate | 414 | 26.85 | 20.7 |
| 7 | 4-(2-Aminoethyl)benzenesulfonyl fluoride hydrochloride | 240 | 98.73 | 25.1 |
| 7 | Benserazide hydrochloride | 294 | 22.05 | 31.7 |
| 7 | Mitoxantrone | 517 | 13.15 | 40.3 |
| 7 | (+)-Brompheniramine maleate | 435 | 27.48 | 29.4 |
| 7 | Acetohexamide | 324 | 42.42 | 16 |
| 7 | Cyproterone acetate | 417 | 27.79 | 16.2 |
| 7 | Calcimycin | 524 | 5.14 | |
| 7 | Clotrimazole | 345 | 20.76 | 21.5 |
| 7 | Captopril | 217 | 18.82 | 32.2 |
| 7 | DL-p-Chlorophenylalanine methyl ester hydrochloride | 250 | 25.83 | 15.6 |
| 7 | Centrophenoxine hydrochloride | 294 | 20.42 | 13.4 |

A potential agent for use in the present methods, acetohexamide, was found have a low level of cytotoxicity and a high priority score (data described below), meaning a high degree of BER activation. Acetohexamide is a sulfonylurea derivative, part of a class of hypoglycemic drugs used for treating diabetes mellitus type 2. These drugs act by increasing the release of insulin from beta cells located in the pancreas. Sulfonylureas have the following basic structure:

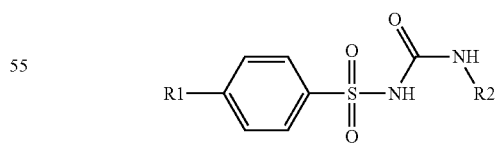

Other sulfonylurea derivatives can include, for example: carbutamide, tolbutamide, acetohexamide, tolazamide, chlorpropamide, glipizide, gliclazide, glibenclamide (glyburide), glibornuride, glisoxepide, glyclopyramide, and glimepiride.

In some embodiments, the DNA repair agent comprises an acetohexamide analogue the following base structural formula:

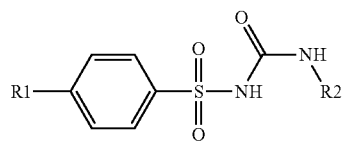

wherein:
R1 is selected from hydrogen, $NH_2$, alkyl (C1 to C20), acetyl; and
R2 is selected from alkyl (C1 to C20) and cyclohexane.

In some embodiments, R1 may either be a methyl group or a 1-oxoethyl group and R2 is a cyclohexyl group, a butyl group, or an isopentyl group.

In some embodiments, the DNA repair agent is acetohexamide, which has the following structure:

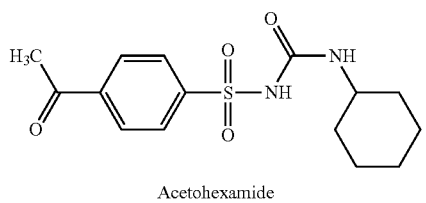 [SMILES: CC(=O)c1ccc(S(=O)(=O)NC(=O)NC2CCCCC2)cc1]

Acetohexamide

In other embodiments of the present invention, structural or functional analogs of acetohexamide may be used as the DNA repair agent. These analogs (termed BA-4, BA-5 and BA-9) are represented below by the following structures:

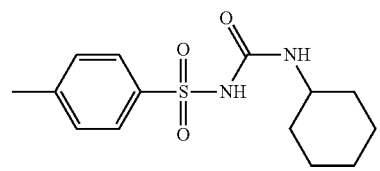

BA-4

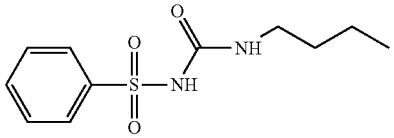

BA-5

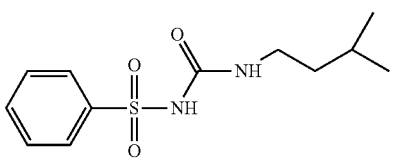

BA-9

Two polymorphic forms of acetohexamide have been characterized. For both polymorphic forms the dissolution rates and solubilities have been investigated. The phosphate buffer (pH 7.6) prescribed in the usp xix as the medium for the dissolution test of acetohexamide tablets cannot be used, because a less soluble potassium salt crystallises during the dissolution process.

In another embodiment, the DNA repair agent may be another sulfonylurea derivative, glipizide, N-(4-[N-(cyclohexylcarbamoyl)sulfamoyl]phenethyl)-5-methylpyrazine-2-carboxamide, which has the following structure:

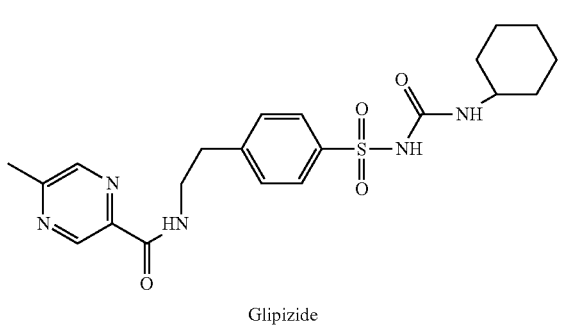 [SMILES: Cc1cnc(C(=O)NCCc2ccc(S(=O)(=O)NC(=O)NC3CCCCC3)cc2)cn1]

Glipizide

In yet another embodiment, the DNA repair agent is benserazide, a decarboxylase inhibitor used in the treatment of Parkinson's disease. Benserazide, DL-Serine, 2-[(2,3,4-trihydroxyphenyl)methyl]hydrazide, also named 2-amino-3-hydroxy-N'-[(2,3,4-trihydroxyphenyl)methyl]propanehydrazide, has the following structure:

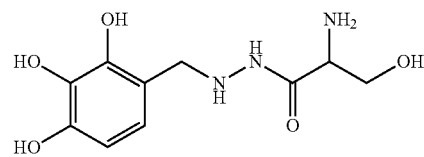

Benserazide

The bensearzide may exist as a salt, DL-Serine 2-(2,3,4-trihydroxybenzyl)hydrazide hydrochloride:

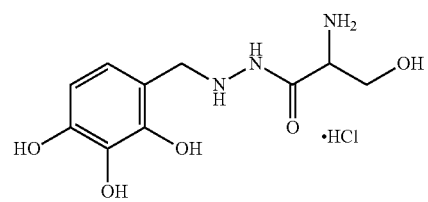 [SMILES: NC(CO)C(=O)NNCc1ccc(O)c(O)c1O ; Cl]

Analogs of benserazide are known, such as

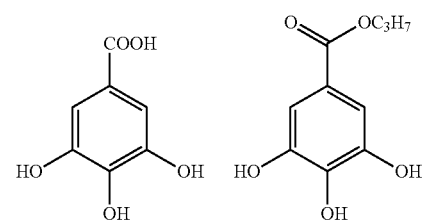

Gallic acid          Propyl gallate

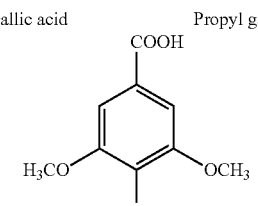

Syringic acid

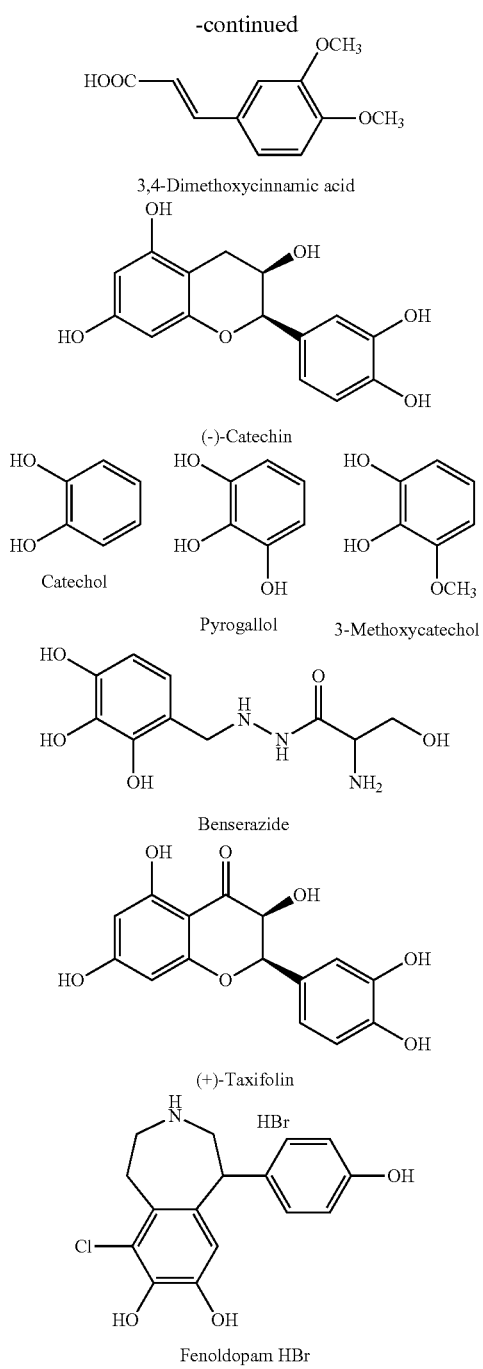

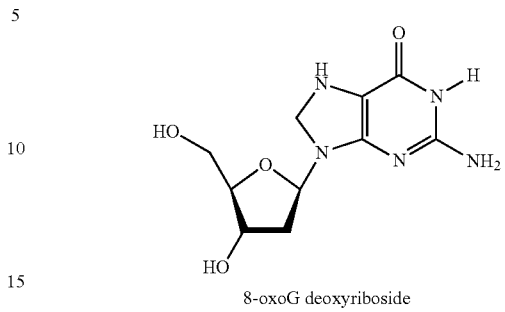

8-oxoG deoxyriboside

These are described in Deng et al., "The Three Catholics Benserazide, Catechol and Pyrogallol are GPR35 Agonists," Pharmaceuticals (Basel). April 2013; 6(4): 500-509. These compounds are referred to herein as "benserazide analogs."

In some embodiments, the DNA repair agents described above may be administered to the patient in combination with each other. Analogs of benserazide may be prepared and tested as described below. Such analogs may have the formula R'—NH—NH—C(=O)—C(NH$_2$)—R", where R' and R" are substituted aryl or alkyl compounds. That is, they have the amine structure depicted above.

Oxidative DNA Damage (ODD)

A common form of oxidative DNA damage is 8-oxo-7,8-dihydroguanine (8-OG), which is the product of the oxidation of guanine. This damage occurs from reactive oxygen species (ROS) and from ionizing radiation. The structure of 8-OG deoxyriboside is shown below:

In order to repair 8-OG, DNA repair enzymes OGG1 (8-oxoguanine glycosylase) and NEIL1 (endonuclease VIII-like 1) excise the damaged base from the DNA strand. OGG1 and NEIL1 are glycosylase enzymes, which upon removal of the damaged base leaves an apurinic (AP) site. The AP site is then cleaved by an AP lyase and removed. The gap created is then filled by additional repair enzymes.

In some embodiments, a single-base alteration resulting in oxidative DNA damage is 5-hydroxyuracil (5-OHU), which is repaired by the enzyme NEIL1. The structure of 5-OHU is shown below:

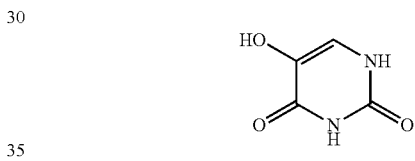

Exemplary Malignancies to be Intercepted

In some embodiments, an inherited or acquired genetic mutation leads to a predisposition to malignancy in a subject. Thus malignancy can be intercepted by administration of one of the compounds disclosed here prior to malignancy develops. Harmful lesions can result in structural DNA damage, such as the 8-OG described above. A cell with an overwhelming amount of damaged DNA may enter into a state of dormancy, undergo apoptosis, or develop into a tumor that is cancerous. Mutations in the genome due to DNA damage are also the cause of many other malignancies. An exemplary, but not exhaustive list of malignancies includes cancers, specifically BRCA1- and BRCA2-associated breast cancers, ovarian cancer, retinoblastoma, various degenerative or sclerotic diseases, including but not limited to Alzheimer's disease, Parkinson's disease, amyotrophic lateral sclerosis, atherosclerosis, ischemic neuronal injuries, TMJ degenerative disease, cataracts, macular degeneration, retinal degeneration, rheumatoid arthritis, multiple sclerosis, or muscular dystrophy. The particular malignancy treated or prevented will be linked to the gene whose lack of repair function gives rise to the malignancy.

Hereditary breast cancers due to mutations in the breast cancer susceptibility gene 1 (BRCA1) are primarily of the basal-like subtype and also tend to be triple-negative. They share similar gene expression patterns, morphologic characteristics, immunohistochemical profiles, and pathologic features with sporadic basal-like breast cancers, including high histologic grade, high mitotic index, overexpression of epidermal growth factor receptor, mutations in p53, and cytogenetic abnormalities.

Hundreds of mutations have been identified in the BRCA1 gene. A listing of BRCA1 susceptibility mutations that would suggest interception by the present methods may be found, e.g. in Olson et al. "Cancer susceptibility mutations of BRCA1," U.S. Pat. No. 6,083,698, issued Jul. 4, 2000. A list of BRCA1 mutations may also be found in the Universal Mutations Database (UMB-BRCA1), found at www(dot)umd.be/BRCA/. Similarly, a list of mutations suggesting the present interception may be found in Lescallett et al, "Cancer susceptibility mutations of BRCA2," U.S. Pat. No. 6,051,379, issued Apr. 18, 2000. The cell line SUM149 contains BRCA1 mutation 2288delT (fs4735X).

Other malignancies described herein are Li-Fraumeni syndrome (also known as Sarcoma, breast, leukaemia, and adrenal gland (SBLA) syndrome) and p53 related mutations. Li-Fraumeni is a syndrome that greatly increases a patient's susceptibility to cancer. The syndrome is linked to germline mutations of the p53 tumor suppressor (TP53) gene and the human checkpoint (CHEK2) gene. The p53 tumor suppressor activates DNA repair proteins, can stop cell growth, and can initiate apoptosis. Mutations in the TP53 gene allow cells to grow and divide uncontrollably to form tumors. These mutations in p53 are often accompanied by mutations in BRCA1. The protein encoded by CHEK2 is a protein kinase that is activated in response to DNA damage. Mutations in CHEK2 cause similar conditions to those of TP53.

In some instances, the malignancies to be intercepted are recurrences of previous conditions. For example, a cancer can recur after a period of time when no cancer could be detected. For example, breast cancer can come back as a local recurrence (in the treated breast or near the mastectomy scar) or somewhere else in the body. The most common sites of recurrence outside the breast include the lymph nodes, the bones, liver, lungs, or brain.

Identification of Candidate Subjects to Receive Preventive Therapy

As noted above, a candidate subject is one for whom it is desired to minimize the likelihood of a recurrence. In addition, a candidate for the present preventive therapy may be one who has had a cancer in one organ and it is desired to prevent a second occurrence in another organ, which may be similar or different organ type. Certain cancers are known to be more likely to recur, as described, for example, in Paik et al., "A Multigene Assay to Predict Recurrence of Tamoxifen-Treated, Node-Negative Breast Cancer," N. Engl. J. Med. 351:2817-2826 (2004). Also, triple-negative breast cancer is associated with a higher risk of local recurrence.

A candidate subject may be identified by genetic testing to identify mutations in the genes described above. A candidate subject may be identified by a likelihood of recurrence. For example, risk for contralateral second primary breast cancers varies substantially by HR status of the first tumor, age, and race and/or ethnicity. Women with HR-negative first tumors have nearly a 10-fold elevated risk of developing HR-negative second tumors, compared with the general population. These findings warrant intensive surveillance for second breast cancers in women with HR-negative tumors. Kurian et al., "Second Primary Breast Cancer Occurrence According to Hormone Receptor Status," J Natl Cancer Inst 2009; 101: 1058-1065.

A candidate subject may be identified by obtaining a cell sample from the subject and testing it for DNA repair using an assay such as described here. Lymphocytes obtained from a standard venipuncture could be used for this purpose. Other testing for lowered DNA repair activity could be carried out as part of a general health assessment. Other assays for detecting a lowered level of DNA repair activity would involve assays for levels of enzymes or enzyme transcripts of enzymes that affect DNA repair in a cell. These include, for example, assaying for levels of glycosylases OGG1, NTHL1, and NEIL1; AP endonuclease APEX1; polymerases POLB (polymerase (DNA directed), beta), POLD (polymerase (DNA directed), delta 1, catalytic subunit); flap-structure-specific endonuclease FEN1; and ligase LIG3 (ligase III, DNA, ATP-dependent). Glycosylases act in a lesion-specific manner to remove oxidatively-damaged bases, and in turn, generate an abasic or apurinic/apyrimidinic (AP) site. AP-endonuclease then cleaves the phosphodiester backbone. In the short-patch pathway, DNA polymerase displaces the AP-site and adds a nucleotide, and then ligase forms a phosphodiester bond to complete repair. In the long-patch pathway, polymerase displaces and adds >1 nucleotide, flap structure-specific endonuclease removes the displaced nucleotides, and ligase completes repair. One or more genes selected from the following table may be tested for a mutation that will affect base excision repair or genomic stability:

TABLE 3

Genes wherein a mutation indicates that a subject is a candidate for the present therapy:

| | |
|---|---|
| APEX1 | APEX nuclease (multifunctional DNA repair enzyme) 1 |
| BARD1 | BRCA1 associated RING domain 1 |
| BRCA1 | breast cancer 1, early onset |
| BRCA2 | breast cancer 2, early onset |
| CHEK1 | checkpoint kinase 1 |
| CHEK2 | checkpoint kinase 1 |
| FEN1 | flap structure-specific endonuclease 1 |
| MUTYH | mutY homolog |
| NEIL1 | nei endonuclease VIII-like 1 (*E. coli*) |
| NEIL2 | nei endonuclease VIII-like 2 (*E. coli*) |
| NTHL1 | nth endonuclease III-like 1 (*E. coli*) |
| NUDT1 | nudix (nucleoside diphosphate linked moiety X)-type motif 1 |
| OGG1 | 8-oxoguanine DNA glycosylase |
| PTEN | phosphatase and tensin homolog |
| PARP1 | poly (ADP-ribose) polymerase 1 |
| TP53 | tumor protein p53 |
| TDG | thymine-DNA glycosylase |
| UNG | uracil-DNA glycosylase |
| XRCC1 | X-ray repair complementing defective repair in Chinese hamster cells 1 |
| XRCC2 | X-ray repair complementing defective repair in Chinese hamster cells 2 |
| XRCC3 | X-ray repair complementing defective repair in Chinese hamster cells 3 |
| XRCC4 | X-ray repair complementing defective repair in Chinese hamster cells 4 |

Other assays may be used in a candidate subject to measure levels of oxidative DNA damage that have occurred due to environmental factors, age, etc. These tests include an OxyFLOW kit (Hemogenix); alkaline comet assay modified for detection of ODD; HPLC/EC; HT 8-oxo-dG ELISA Kit for the detection and quantitation of 8-hydroxy-2'-deoxyguanosine in urine, serum and saliva samples (Trevigen Catalog #4370-096-K).

A candidate subject may also be identified on the basis of a family history of a serious disease warranting the preventive therapy.

Dosage and Formulation

The DNA repair agents may be administered in a standard manner for example, by oral or parenteral administration. For these purposes they may be formulated by means known to the art into the form of, for example, tablets, capsules, pills, powders, aqueous or oily solutions or suspensions, emulsions, and sterile injectable aqueous or oily solutions or suspensions. Other means of administration include, for example, buccal delivery; sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, EP0445920, EP0722324, EP0091193, U.S. PG Pub. 2004/0034016, U.S. Pat. Nos. 4,826,875, 5,017,607, 6,540,983, as well as in patents cited therein.

The formulations of the present invention may conveniently be presented in unit dosage form and may be prepared by any methods well known in the art of pharmacy. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, out of one hundred percent, this amount will range from about 1 percent to about 99 percent of active ingredient, in some embodiments from about 5 percent to about 70 percent, and in more specific embodiments from about 10 percent to about 30 percent.

The DNA repair agents suitable for administration may be prepared by mixing the effective ingredient with a pharmaceutically acceptable used carrier, excipient, binder, stabilizer and the like, which are well known in the art. A unit dose formulation such as a tablet or capsule will usually contain 1-500 mg of a DNA repair agent, such as a sulfonylurea derivative.

The pharmaceutical compositions of this invention may be administered up to six times daily, conveniently 1 to 4 times daily, so that a dose of the DNA repair agent or pharmaceutically acceptable salt thereof in the general range 0.02-60 mg/kg, preferably 0.1-20 mg/kg, is administered daily. It will be appreciated by those skilled in the art that the dosage will necessarily be varied as appropriate, according to the severity of the condition under treatment, according to the age and sex of the patient and according to known medical principles. In addition, account should be taken of the recommended maximum daily dosages for the DNA repair agent; for example, for acetohexamide this may be in the region of 1.5 g.

The compounds disclosed as DNA repair agents herein may be formulated with a variety of pharmaceutically acceptable materials, compositions, and/or dosage forms that are within the scope of sound medical judgment, suitable for use in contact with the tissues of human beings and animals without excessive toxicity, irritation, allergic response, or other problem or complication, commensurate with a reasonable benefit/risk ratio.

The pharmaceutically acceptable material, composition, or vehicle, such as a liquid or solid filler, diluent, excipient, solvent, or encapsulating material, is involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See *Remington: The Science and Practice of Pharmacy*, 20th ed. (Alfonso R. Gennaro ed.), 2000.

Methods and Materials of Examples 1-11
Screening Reagents

Reagents for the screen included adenovirus containing an oxidatively damaged GFP reporter gene and Hoescht 33342 live cell dye. Adeno-X™ acGFP marker virus (adGFP; Clontech) was amplified, purified, and titered using the Adeno-X Mega Purification kit (Clontech) according to the manufacturer's instruction. Oxidative DNA damage to adGFP was carried out by photodynamic treatment (PDT) as previously described in Alli et al., Cancer Res 69, 3589-3596 (2009), with the exception of PDT being for 2 minutes, which increased the dynamic range for GFP signal output. The new PDT conditions were confirmed to produce ODD and not damage to the viral capsid, which would otherwise prevent viral entry into the cell and result in poor screening outcome (data not shown). Hoechst 33342 was purchased from Sigma-Aldrich® and prepared according to the manufacturer's instruction.

HT Chemical Screen

On day 0, 750 cells were seeded (500/well) in 384-well black-wall/clear bottom tissue-culture treated plates using a WellMate® microplate dispenser (Matrix) and allowed 24 hours to adhere and begin cycling. On day 1, controls and compounds were added using a Sciclone ALH3000 Workstation (Caliper Life Sciences) operating in a fully automated mode. DMSO (negative control) or 18 µM BrdU (positive control) were delivered at 5 ul/well to columns 1-2 and 23-24, respectively; compounds were transferred at 100 nl/well to columns 3-22 using a 384 Pin Tool (V&P Scientific, Inc.) attached to the workstation. Cells were incubated with compound for 24 hours. On day 2, oxidatively damaged ad-GFP was added to all wells in 10 µl volume using the WellMate® microplate dispenser, and then allowed 24 hours for host-cell reactivation (HCR). On day 3, following the addition of 2 ug/ml Hoechst 33342 live-cell dye (5 µl/well) using the WellMate® microplate dispenser and incubation for 30 minutes, fluorescence was measured by imaging with the ImageXpress Micro high-content imager (Molecular Devices) with built-in ABC correction and by plate reading using the Analyst GT Multimode Reader (Molecular Devices, Inc.). Acquisition of data by imaging included the detection of GFP expression (Ex 485±20 nm/Em 525±30 nm) and Hoechst staining (Ex 387±11 nm/Em 440±40 nm) at two different sites per well followed by quantification using MetaXpress software equipped with the Cell Scoring module.

Post-Screen Analysis

GFP expression obtained by imaging and plate reading was normalized to Hoechst 33342 staining, and expressed as '% GFP-positive cells' and 'GFP intensity', respectively. The 'percentage of GFP-positive cells' was calculated relative to the percentage of Hoechst-positive cells, i.e. % GFP-positive cells=GFP (+)/Hoechst 33342 (+). Acquisition of data by plate reading included the bottom-read detection of GFP expression (Ex 475/Em 505, Cutoff 495) and Hoechst staining (Ex 350/Em 450, Cutoff 435) using Soft-Max Pro software. 'GFP intensity' was calculated relative to Hoechst intensity, i.e. GFP Intensity=GFP (F.U.)/Hoechst 33342 (F.U.). For both methods of detection, the '% BER Activity' and $EC_{50}$ values (when available) were calculated using Assay Explorer software from Accelrys Software, Inc.

Cell Lines

Human breast cancer cell lines that were deficient in BER (HCC1143, MDAMB468, HCC1937, and SUM149) or proficient in BER (BT474 and MCF7) were cultured according to American Type Culture Collection guidelines, with the exception of SUM149, which was cultured according to Asterand plc guidelines. $Brca1^{+/+}$ and $Brca1^{-/-}$ mouse mammary epithelial cells (MMECs) were previously described.

SUM149 and HCC1937 cell lines harbor a BRCA1 mutation. HC1143 and MDAB468 cell lines represent the basal-like subtype of breast cancer. BRCA1-mutated and basal-like breast cancers share similar characteristics, including compromised ability for BER of ODD. All of these cell lines were experimentally determined to have defective BER of ODD.

DNA Repair-Activating Agent Treatment

Cells were treated with DMSO (vehicle control) or acetohexamide or benserazide as indicated for 24 hours at 37° C. and 5% $CO_2$.

DNA Repair Assay

The DNA repair assay was carried out as described in the examples below. Where indicated, BER (base excision mode of DNA repair) activity was expressed relative to the control (DMSO).

8oxoG Lesions

Cells were analyzed using the OxyFlow™ Kit (Hemogenix) according to the manufacturer's instructions.

Alkaline Comet Assay

Cells were collected and embedded into CometAssay® LM Agarose (Trevigen) and placed on CometAssay® HT Slides (Trevigen) in duplicate. Cells were lysed at 4° C. in Lysis Buffer (Trevigen) for >24 hours. Slides were treated with or without FPG enzyme at 37° C. and 5% $CO_2$ for 45 minutes to nick DNA at sites of ODD and then subjected to alkaline treatment at 4° C. for 40 minutes to denature DNA. Slides underwent electrophoresis under alkaline conditions to separate intact from damaged DNA. Following neutralization, DNA was stained using SYBR® green I and visualized as a comet in shape by fluorescent microscopy under 20× objective. Tritek CometScore software was used to quantify % DNA in Tail. Strand breaks were determined by % DNA in Tail in FPG-minus samples. ODD was determined by subtracting % DNA in Tail in FPG-minus samples from % DNA in Tail in FPG-plus samples.

Hoechst 33358 Live-Cell Staining

Cells were treated with acetohexamide for 48 hours in quadruplicate and then incubated with 2 μg/ml Hoechst 33358 live-cell dye for 20 minutes. Four representative fields for each replicate were imaged by the ImageXpress 5000A high-content imager (Molecular Devices). Nuclei were counted using MetaMorph® software (Molecular Devices) and expressed as a percentage relative to the vehicle control (DMSO).

MTT Assay

Cells were treated for 72 hours and analyzed as described in Alli et al., Cancer Res 69, 3589-3596 (2009).

Acetohexamide Analogs

Glipizide, a compound within the LOPAC library, was re-ordered from Sigma-Aldrich. BA-4, BA-5, and BA-9 were synthesized by independent laboratories and purchased from eMolecules. Then, BA4, BA-5, and BA-9 were sent to the Stanford Mass Spectrometry Facility for MW confirmation by LC-MS analysis.

Statistical Analysis

Statistical analysis was carried out using the student's two-tailed t-test with the exception of the DNA repair assay, which utilized the student's one-tailed t-test.

EXAMPLES

Example 1: Identifying DNA Repair Agents by Chemical Library Screening

Figure 3A:
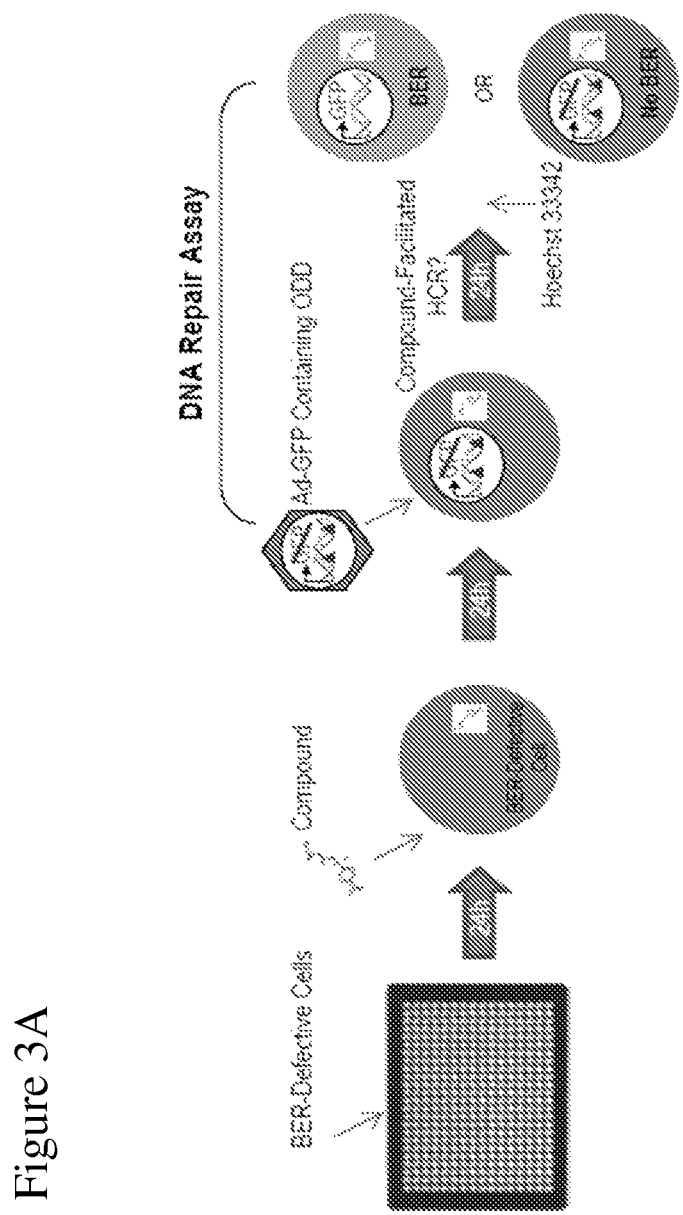
FIG. 3A is a schematic showing the 4 steps of a high-throughput (HT) screen protocol to identify small molecules that enhance base excision repair of oxidative DNA damage.

To identify molecules that activate repair of ODD, we screened a chemical library using a DNA repair assay. The screening protocol consisted of four steps:
(1) plating of BER-defective cells;
(2) addition of compounds (or controls);
(3) the DNA repair assay;
(4) addition of Hoechst 33342 live-cell dye (to allow for normalization to cell number) prior to fluorescent detection by image analysis and plate reading (FIG. 3A).

The DNA repair assay provides the advantage of evaluating BER of ODD while maintaining an intact cellular environment, which is superior to previous assays that have been limited by specificity and in vitro analyses. The cell-based DNA repair assay is an activation assay that is ideal for high-throughput use due to its requirement for only a single-reagent transfer step and fluorescent read-out.

Briefly, cells of interest are transfected with an ODD-containing GFP reporter gene (as described above). An adenovirus containing a GFP reporter gene was given a photodynamic treatment, which is known to deliver oxidative damage. Given that the virus consists of two macromolecules: protein (viral capsid) and DNA, PDT conditions that delivered oxidative DNA damage and not protein damage were experimentally determined. Therefore, the adenoviral DNA treated with PDT is equivalent to the "ODD-containing GFP reporter gene". It is the repair that is either defective or not defective, not the reporter gene. Defective repair is relative, i.e. SUM149 cells are defective in repair relative to MCF7 cells via adenoviral-mediated gene transfer, allowed sufficient time to carry out repair of the reporter gene, and then analyzed for fluorescence. Expression of GFP indicates repair (see FIG. 1 and discussion below).

Example 2: Defining the Cell Line, Identifying Controls, and Preparing the Chemical Library SUM149 human breast cancer cell line was chosen due to its ability for adenoviral infectivity (required for delivery of the ODD reporter) and its inability to effectively repair ODD (required for detection of compound-facilitated BER) (FIG. 1).

Figures 2A, 2B, 2C:
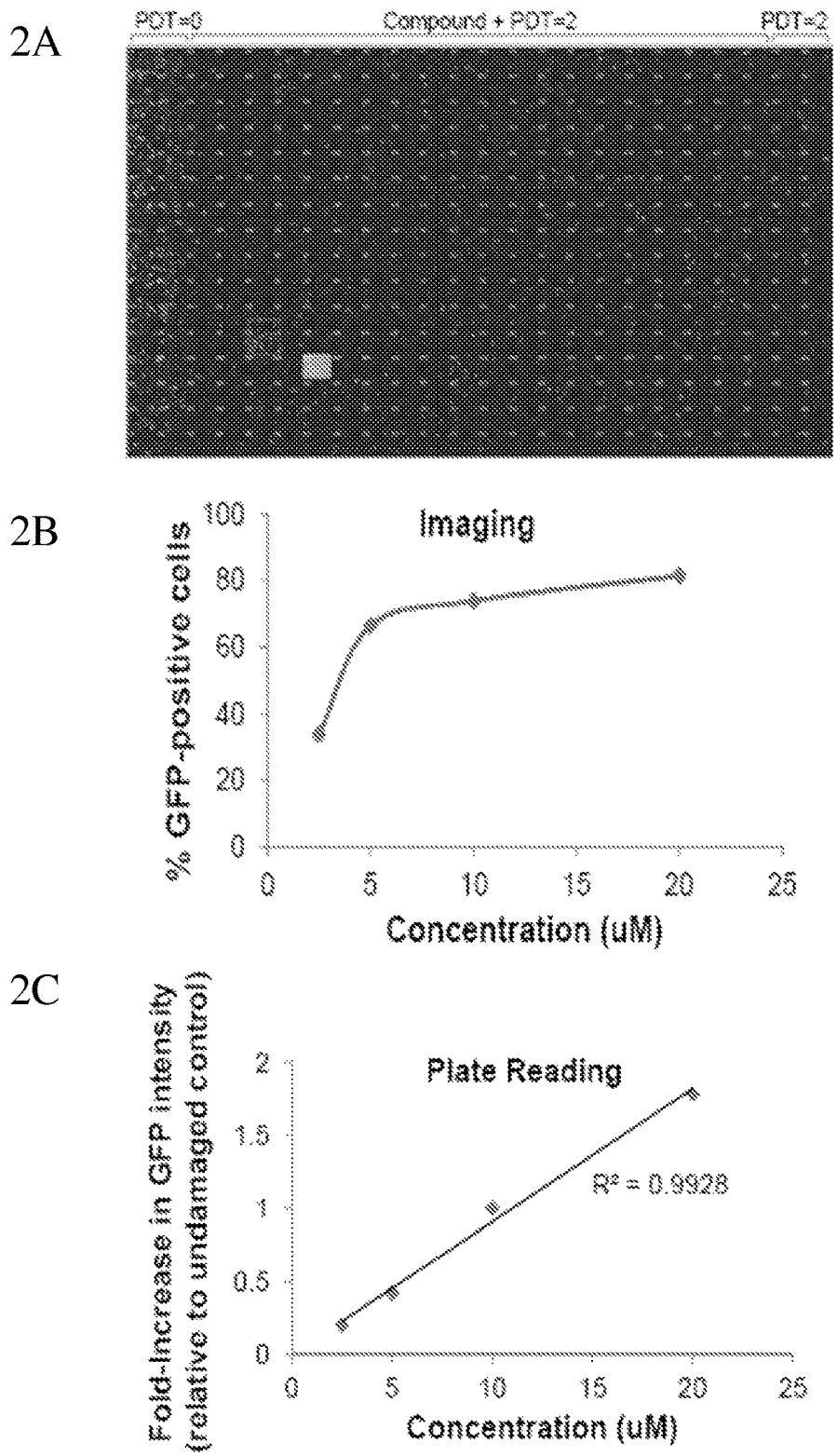
FIG. 2A, 2B, 2C are an image and two line graphs showing the results of a preliminary screen of BrdU as a small molecule control.

DMSO served as the negative control and 18 μM BrdU functioned as the positive control. We identified BrdU in a preliminary screen (FIG. 2A-2C) due to the lack of an existing but necessary small-molecule positive control. The molecule that produced the greatest GFP signal was defined as the small-molecule positive control. A montage of the images obtained from the 384-well plate at the highest concentration tested (18 uM) is shown (FIG. 2A). BrdU produced a visible signal similar to that of SUM149PTcells infected with undamaged adGFP. BrdU produced a dose-response increase in the percentage of GFP-positive cells (normalized to the number of Hoechst 33342-positive cells) (FIG. 2B). BrdU produced a dose-response increase in GFP intensity (normalized to Hoechst 33342-intensity) (FIG. 2C).

The LOPAC[1280]™ library (Sigma-Aldrich™), which consisted of 1280 compounds with known pharmacological activity, was screened in quantitative high-throughput (qHT) format starting at a 20 µM final concentration of compound in each well (0.1% DMSO) followed by up to six (two-fold) dilutions. Using our HT-protocol, we screened the LOPAC library using SUM149PTcells infected with undamaged ad-GFP as the positive control and SUM149PT cells infected with damaged ad-GFP as the negative control. Compounds were supplied as described by the manufacturer, and then arrayed individually in 384-well plates to produce a total of 28 plates (i.e. 4 plates of compounds, each at 7 different concentrations). The quality of all compounds was assured by the vendor as greater than 90% pure with provided quality control data and was verified internally on 5% random sampling. Additional information about the library, including compound names, functional activity, and structure may be found at www (dot)sigma.aldrich.com.

Example 3: Optimization of Conditions for HT-Screening

Seeding Density

Cells were first plated in black-wall, clear-bottom, 384-well plates at 4000 cells/well followed by 1:1 serial dilutions. Seeding density was defined to produce logarithmically growing cells after 4 days, which is consistent with the timing for the HT-screen, and was determined to be 750 cells/well (data not shown).

Determination of MOI

SUM149PT cells were then seeded as described above and subjected to the screening protocol using mock reagents, but were infected with ad-GFP at M.O.I.=100 pfu/cell followed by 2-fold serial dilutions. Infections were carried out in duplicate. Optimal MOI was defined as the lowest amount of virus that delivered the greatest fluorescent signal by high-content imaging, and was determined to be 50 pfu/ml, which is within the range specified by the manufacturer (i.e. 10-100 pfu/ml) (data not shown).

Optimization of Hoechst 33342

SUM149PT cells were seeded as described above and subjected to the screening protocol using mock reagents, but were stained using 5 µg/ml followed by 1:1 serial dilutions of Hoechst 33342. Optimal Hoechst 33342 concentration was defined to produce a significant signal above background for the complete population of cells and was determined to be 2 µg/ml (data not shown).

Example 4: Validation of the HT-Screening Protocol

Signal Calculations

On day 0, cells were seeded in 384-well black-wall/clear bottom plates. On day 1, cells were treated with 18 uM BrdU (small-molecule positive control) or DMSO (vehicle, negative control), alternating every 4 columns. On day 2, cells were infected with ad-GFP subjected to PDT for 2 minutes. On day 3, fluorescence was measured using MetaXpress software (Molecular Devices). GFP expression was calculated as % GFP-positive cells (GFP-positive cells/Hoechst 33342-positive cells×100) to determine CV, S/B, and Z'-factor.

Spatial Uniformity Assessment

Figures 4A, 4B:
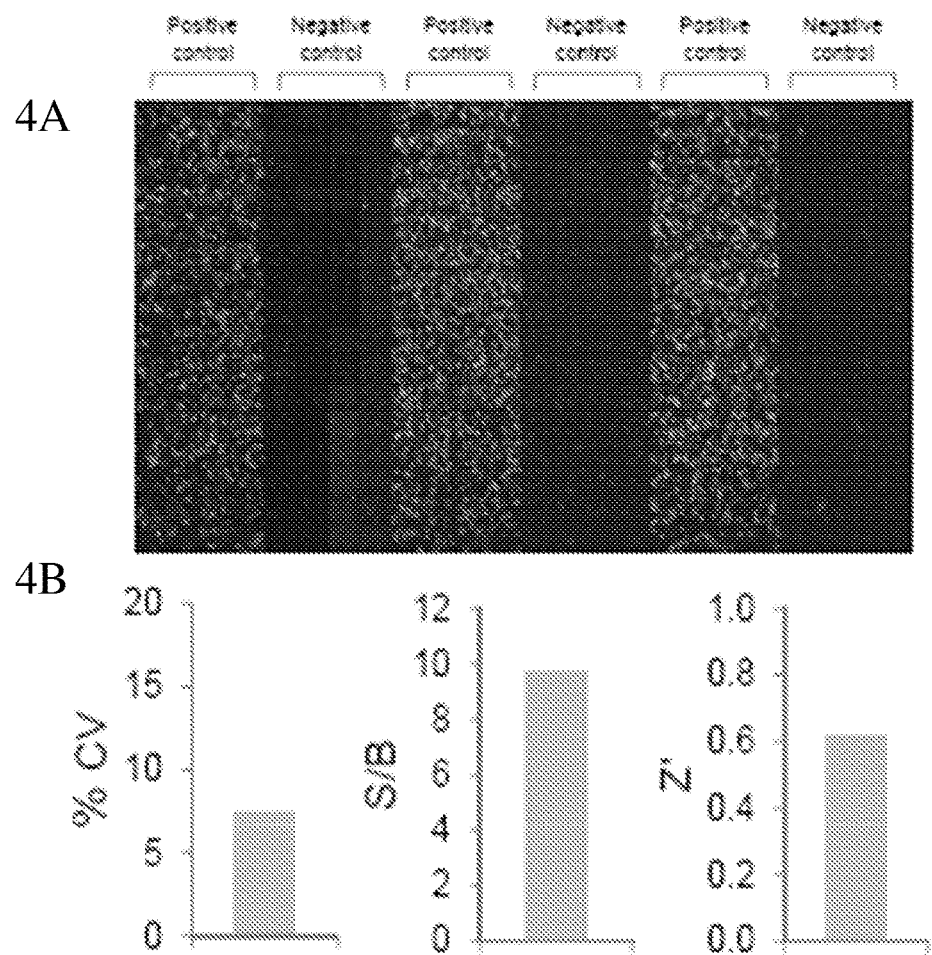
FIG. 4A, 4B is an image and a set of bar graphs showing the validation of the HT screening protocol.
Figures 4C, 4D:
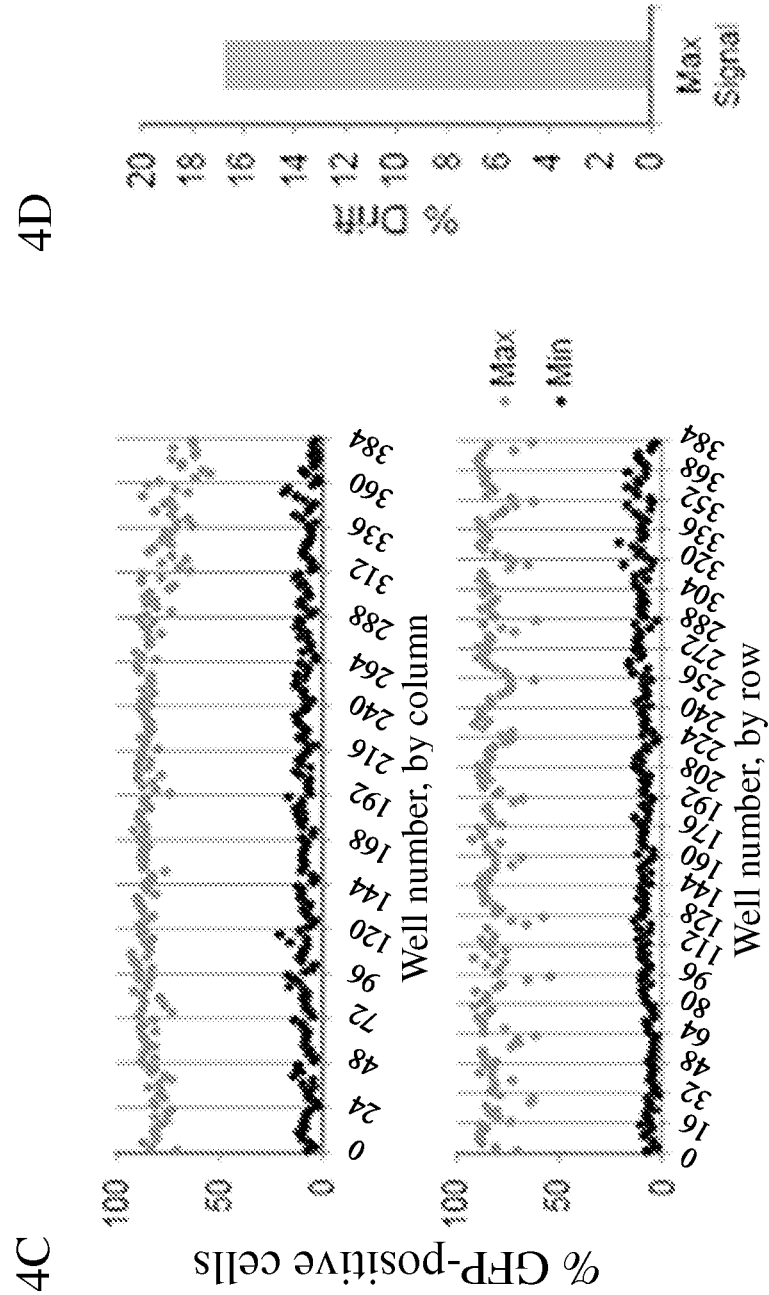
FIG. 4C, 4D is a pair of scatter plots and a bar graph showing an assessment of spatial uniformity.

Scatter plots (FIG. 4C) reveal the number of GFP-positive cells for each positive control well (i.e. max signal; gray) and negative control well (i.e. min signal; black) arranged by row, then column (top) or by column, then row (bottom). No drift or edge effects were observed as evidenced by the lack of a significant trend in signal from left-to-right and top-to-bottom. Percent drift was calculated from the max signal.

Acceptance Criteria

Observed values for each validation parameter were compared to the accepted criteria as defined by the NIH Assay Guidance Manual for high-throughput screening. Results are shown in Table 4, below. All values were within acceptable range.

TABLE 4

| Validation Parameters | | |
|---|---|---|
| Parameter | Acceptance criteria | Observed |
| CV | ≤20% | 7% |
| S/B | ≥5 | 10 |
| Z' | ≥0.4 | 0.6 |
| Edge, drift or other spatial effects | None | None |

Figure 3B:
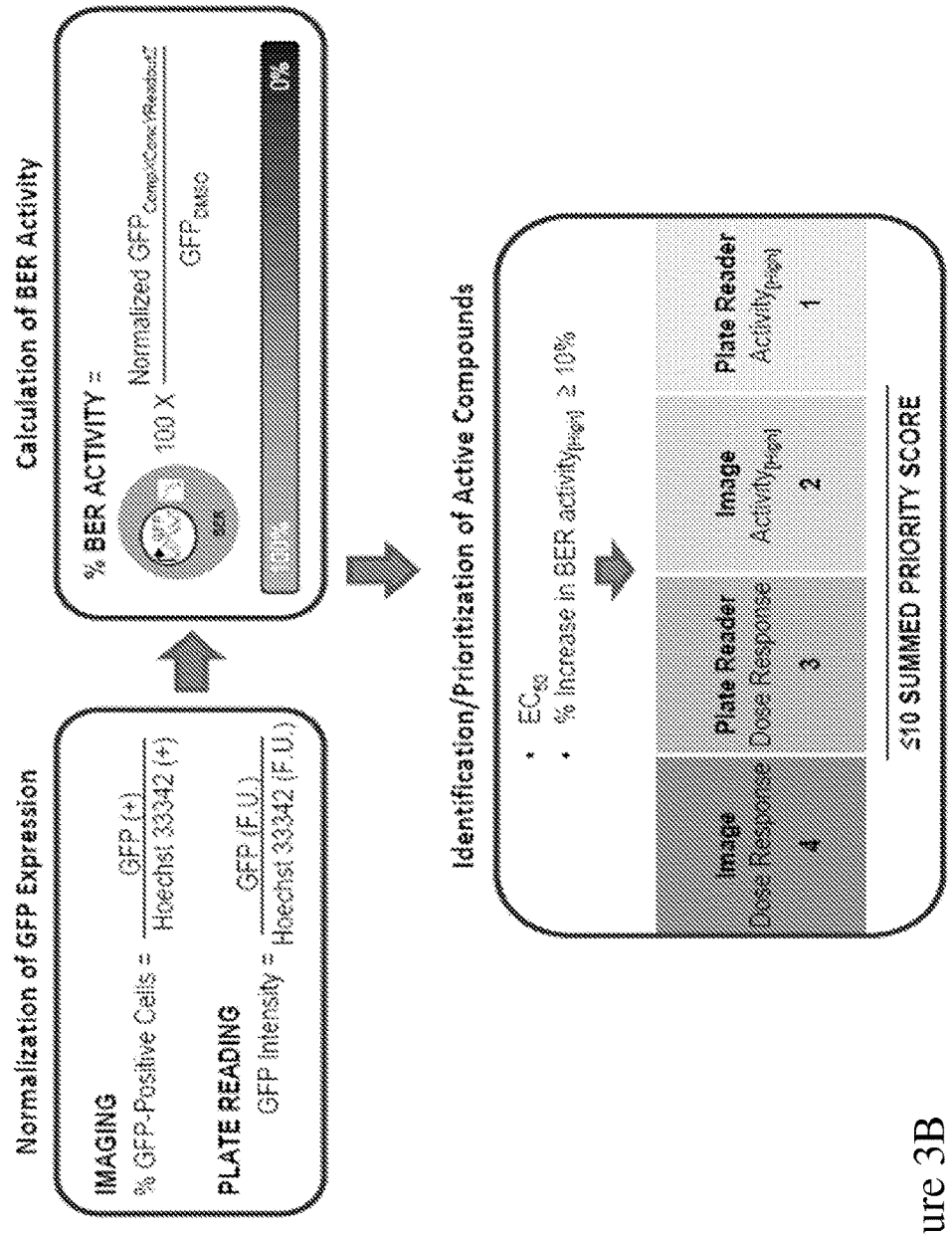
FIG. 3B is a schematic showing the post-screen analysis including the normalization of GFP expression for each well, calculation of the '% BER activity' relative to the negative control, and identification and prioritization of active compounds.

The protocol, as depicted in FIG. 3A-3B, produced a Z'-factor=0.6, CV=7%, S/B=10, and no significant edge or drift effects (FIG. 4A-4D).

Example 5: HT-Screening and the DNA Repair Assay of SUM149PT Cells

A chemical screen in 384-well qHT-format was conducted using the validated protocol described above. SUM149PT cells were treated with up to seven doses of compound (or control), subjected to the DNA repair assay, and assessed for GFP expression by two different means (i.e. imaging and plate reading). Screening took place as one round (i.e. seven concentrations of 1 of 4 compound plates) per week for four weeks. A summary of the HT-screen is given below in Table 5:

TABLE 5

HT-Screen

| Day | Parameter | Volume (μl) | Incubation Time | Description |
|---|---|---|---|---|
| 0 | Plating of BER-defective cells | 60 | 24 h | SUM149PT cell line, 750 cells/well, black-well/clear-bottom tissue culture plates |
| 1 | Addition of controls or | 5 | 24 h | DMSO (−); 18 uM BrdU (+) |
|   | Addition of library compounds | 0.1 | 24 h | LOPAC-1280TM (Sigma Aldrich), 20 μm to 0.3 μM in (two-fold) dilutions |
| 2 | DNA repair assay | 20 | 24 h | (1) Adenoviral-mediated delivery of ODD-containing GFP reporter and (2) host cell reactivation |
| 3 | Staining of live cells | 5 | 30 min | 2 μg/ml Hoechst 33342 |
|   | Detection by imaging | NA | NA | GFP (Ex 485 ± 20 nm/Em 525 ± 30 nm), Hoechst 33342 (Ex 387 ± 11 nm/Em 440 ± 40 nm) |
|   | Detection by plate reading | NA | NA | GFP (Ex 475/Em 505, Cutoff 495), Hoechst (Ex 350/Em 450, Cutoff 435); bottom-read |

Example 6: Post-Screen Analysis

We then identified and prioritized active compounds based on their ability to enhance BER of ODD using a priority scoring system (FIG. 3B). The scoring system consisted of assigning 'priority scores' based on the level of significance of each method of detection and calculating a 'summed priority score' that ranged from 1-10 for each molecule; higher scores indicated higher priority. Greater normalized GFP expression indicated greater enhancement of repair. For both methods of detection (readout), the '% BER Activity' for each compound (comp) at each concentration (conc) was calculated. Active compounds were defined as having produced a dose-response increase in GFP expression ($EC_{50}$) or having increased GFP expression greater than 10% over the negative control at either of the two highest concentrations tested (activity$_{[High]}$). To prioritize active compounds, each molecule was assigned up to four priority scores that reflected the significance of the calculation and method of detection (i.e $EC_{50}$>activity$_{[High]}$ and imaging >plate reading). The assigned priority scores were then summed for each molecule to generate a 'summed priority score' that totaled ≤10 (4+3+2+1), with 10 reflecting the highest priority. For example, a molecule that showed a dose-response increase in BER activity by imaging and plate reading received a priority score of 4 and 3, respectively, and its 'summed priority score' equaled 7.

Figure 5A:
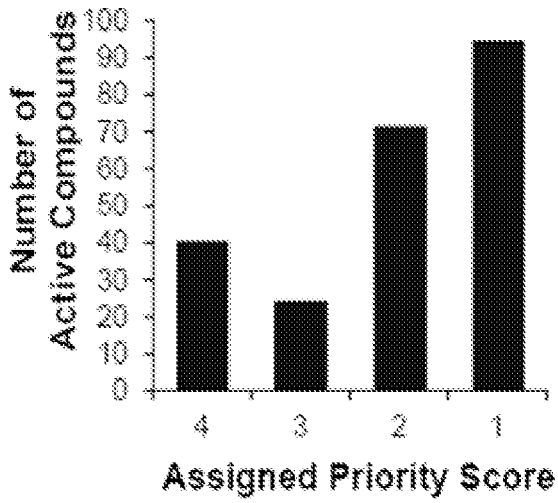
FIG. 5A, 5B is a pair of bar graphs showing the screening outcomes of potential DNA repairing agents. Molecules that were assigned at least one priority score were deemed active compounds. Each bar represents the number of active compounds that were assigned to each of the four priority scores (FIG. 5A). The assigned priority scores 4-1 are as follows: 4 is the score for a molecule showing a dose-response increase in GFP expression by imaging, 3 is the score for a molecule showing a dose-response increase by plate reading, 2 is the score for a molecule showing increased GFP expression at high concentration by imaging, and 1 is the score for a molecule showing increased expression at high concentration by plate reading.
Figure 5B:
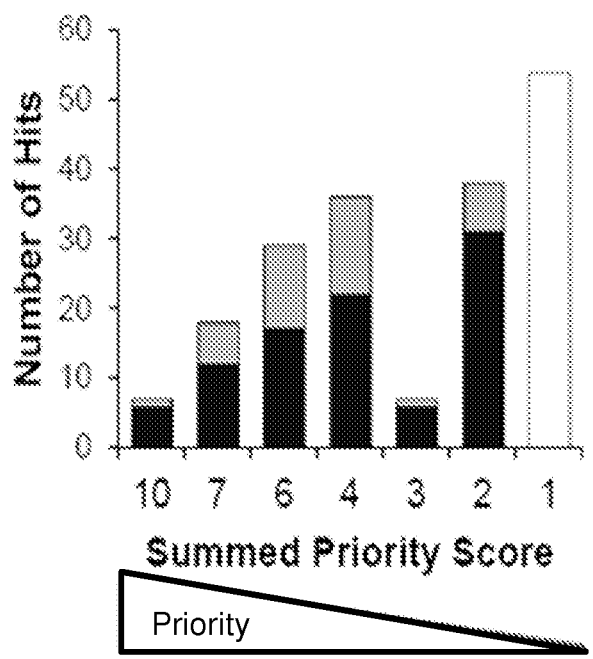

FIGS. 5A-5B depict the number of molecules for each assigned 'priority score' and 'summed priority score', respectively. In general, the number of molecules increased as the score decreased (FIG. 5A). The high prevalence and low priority of molecules with a summed priority score=1 resulted in their elimination; remaining molecules were defined as hits.

Figure 6:
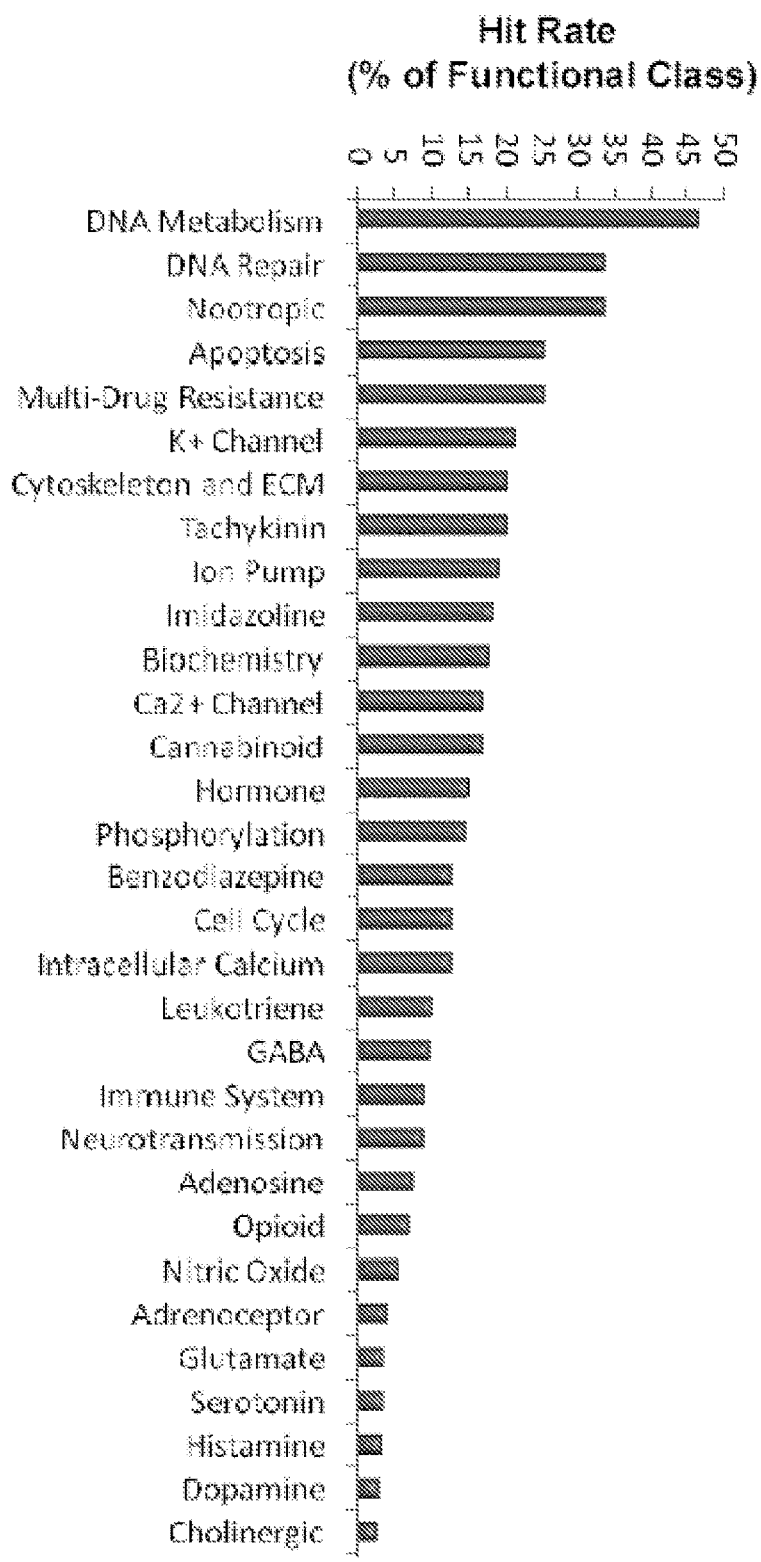
FIG. 6 is a bar graph showing the functional class of each molecule within the compound library as defined by the manufacturer. Each bar represents the hit rate for each functional class, where the hit rate=100×(# of hits in a functional class)/(# of library compounds in a functional class).

We identified 94 molecules (Table 1) that potentially enhanced BER of ODD (hit rate=7.3%). Evaluation of the functional classes of these compounds revealed the greatest percentage of hits as having activity in DNA metabolism or DNA repair (FIG. 6). Given that cytotoxic compounds may be undesirable for some applications, we used our screening data acquired by imaging to identify compounds that decreased the number of Hoechst-positive cells by >20% compared to the negative control. Elimination of these potentially cytotoxic compounds resulted in a subset of 49 hits (hit rate=3.8%). Results for all 94 hits have been provided in Table 1. Detailed results, including the $EC_{50}$ and % BER activity at high concentrations (for each method of GFP detection), the 'summed priority score', % Hoechst-positive cells, and functional class are not shown.

Example 7: Analysis of Acetohexamide and Benserazide

Figure 7A:
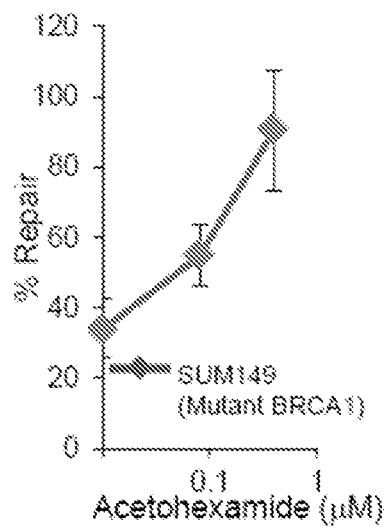
FIG. 7A, 7B is a line graph and bar graph depicting the effect of acetohexamide on BER of an oxidatively-damaged GFP-reporter gene in SUM149 cells (FIG. 7A) and in cell lines with defective or proficient BER (FIG. 7B).
Figure 7B:
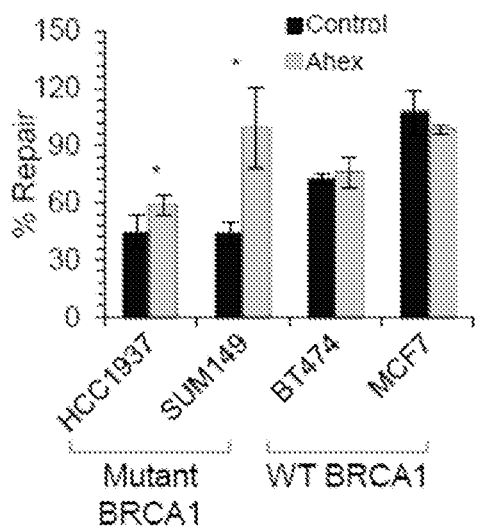
Figure 9:
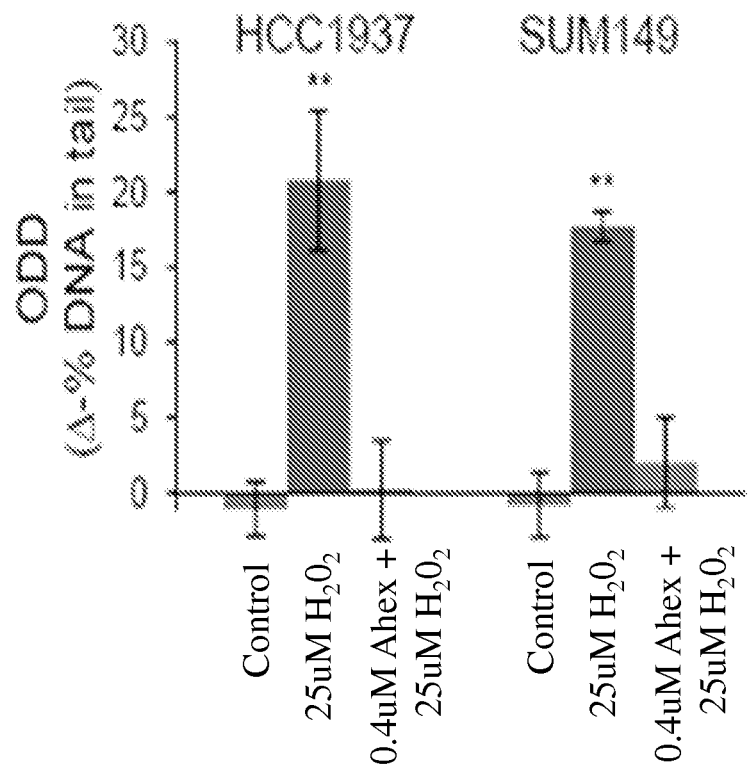
FIG. 9 is a bar graph showing repair of $H_2O_2$-induced levels of ODD following pretreatment with or without acetohexamide compared to undamaged control. The alkaline comet assay modified for detection of oxidative lesions was used. Error bars represent s.e.m.

We further analyzed one of the hits, acetohexamide, chosen for its high priority (summed priority score=7), minimal cytotoxicity (Hoechst-positive cells=87.8%), and commercial availability. To validate activity, acetohexamide was re-ordered from the original vendor and analyzed for BER activity and ODD levels. Acetohexamide produced a dose-response increase in repair of an oxidatively damaged GFP reporter gene in SUM149PT cells (FIG. 7A). Treatment of mutant BRCA1-containing cell lines with 20 μM acetohexamide, i.e. the highest concentration used in the HT-screen, produced a statistically significant increase in BER (HCC1937, p=0.01; SUM149, p=0.007), whereas the same treatment in wild-type BRCA1-containing cell lines exhibited no effect on BER (BT474, p=0.4; MCF7, p=0.1) (FIG. 7B). Acetohexamide also decreased basal levels of 8oxoG lesions, i.e. the most common form of ODD, in a time-dependent manner, and decreased $H_2O_2$-induced ODD to levels similar to those of the undamaged control in breast cancer cell lines with defective BER (FIG. 9). Taken together, these data suggest that acetohexamide enhances BER of ODD.

Figure 8A:
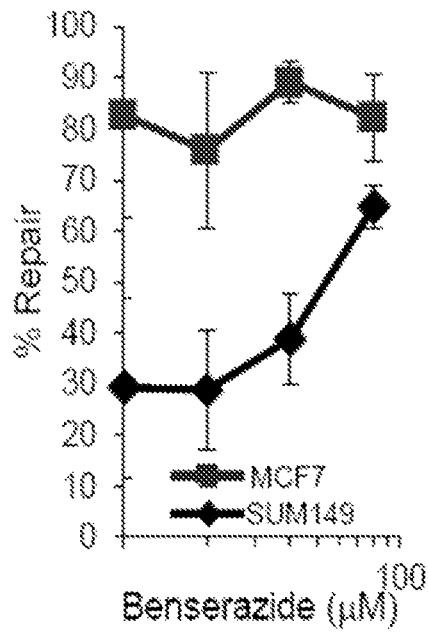
FIG. 8A, 8B is a line graph (8A) and bar graph (8B) depicting the effect of benserazide on BER of an oxidatively-damaged GFP-reporter gene in MCF7 and SUM149 cells (FIG. 8A) and in cell lines with defective or proficient BER (FIG. 8B).
Figure 8B:
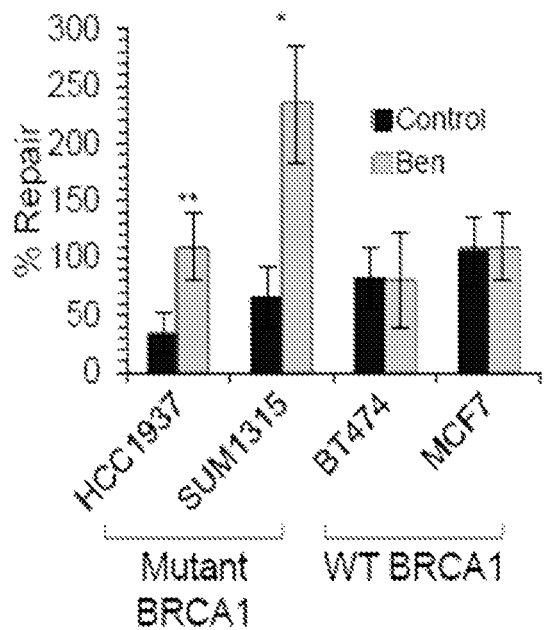

Likewise, benserazide produced a dose-response increase in repair of an oxidatively-damaged GFP reporter gene in SUM149PT cells but not in wild-type BRCA1-containing MCF7 cells (FIG. 8A). Additional breast cancer cell lines displayed similar results (FIG. 8B) using the same assay. Treatment of mutant BRCA1-containing cell lines with 20 μM benserazide produced a statistically significant increase in BER (HCC1937, p=0.007; SUM149, p=0.01), whereas the same treatment in wild-type BRCA1-containing cell lines exhibited no effect on BER (BT474, p=0.3; MCF7, p=0.5) (FIG. 8B).

Example 8: Cytotoxicity of Acetohexamide

Figure 10A:
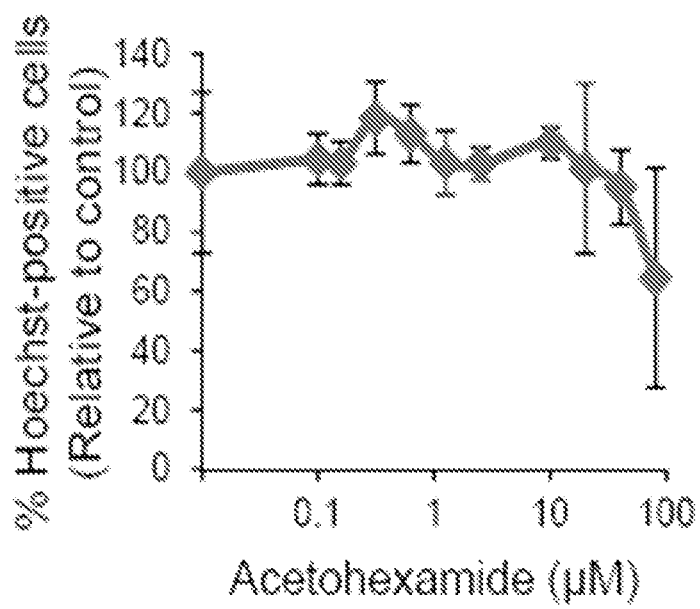
FIG. 10A, 10B is a set of graphs displaying the percentage of live SUM149 cells treated with increasing concentrations of acetohexamide (FIG. 10A) and other BER-defective cells treated with 20 µM acetohexamide (FIG. 10B) as determined by Hoechst 33342 staining. For the latter, error bars represent s.e.m.
Figure 10B:
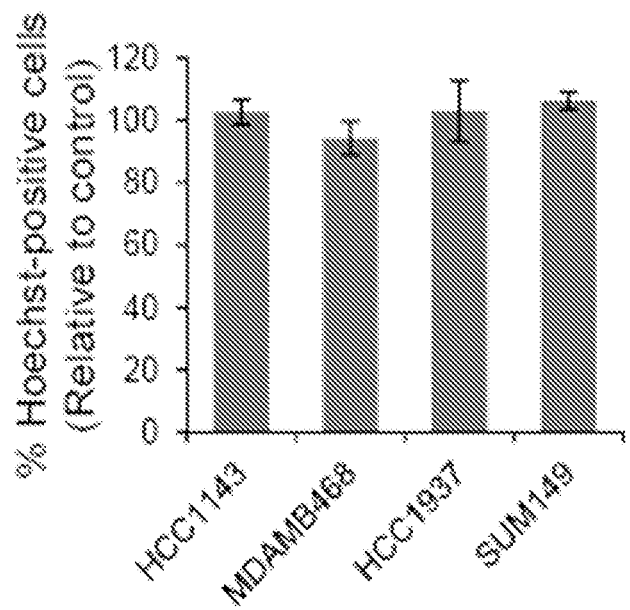
Figure 11:
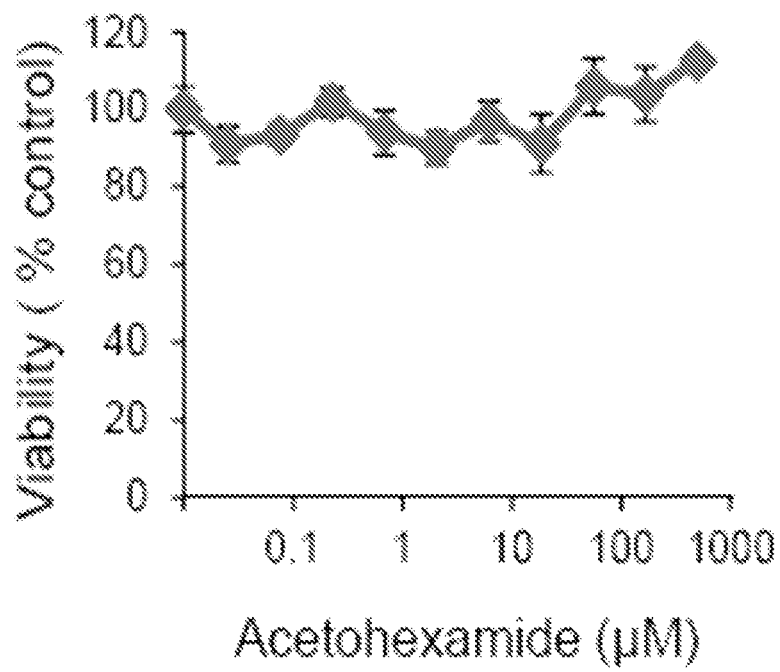
FIG. 11 is a line graph showing the effect of acetohexamide on cell viability of SUM149 cells as shown by MTT assay.

We further evaluated the effect of acetohexamide on cytotoxicity. As determined by Hoechst 33342 staining, acetohexamide did not affect the number of SUM149PT cells at concentrations up to 40 µM (FIG. 10A), nor did it affect the cell number of other BER-defective breast cancer cell lines at 20 µM (FIG. 10B). MTT assay confirmed these data; acetohexamide did not affect the cell viability of SUM149PT and other cell lines at concentrations up to 1 mM (FIG. 11 and data not shown). Therefore, BER-activating concentrations of acetohexamide were not cytotoxic, which is consistent with in vitro and in vivo reports.

Example 9: Acetohexamide's Effect on Ber Activity

Figure 12A:
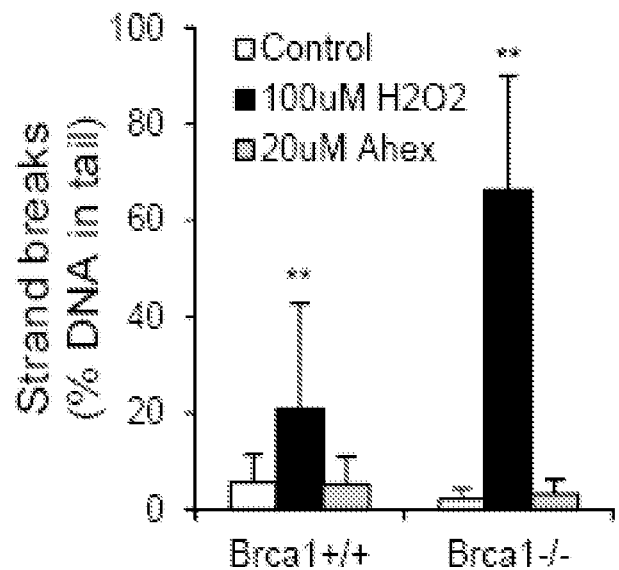
FIG. 12A, 12B is a pair of bar graphs showing the strand breaks, measured by alkaline comet assay, in $Brca1^{+/+}$ (BER-proficient) and $Brca1^{-/-}$ (BER-deficient) MMECs treated for 16 hours as indicated (FIG. 12A) and in human breast cancer cell lines with defective BER treated for 4 hours as indicated (FIG. 12B).
Figure 12B:
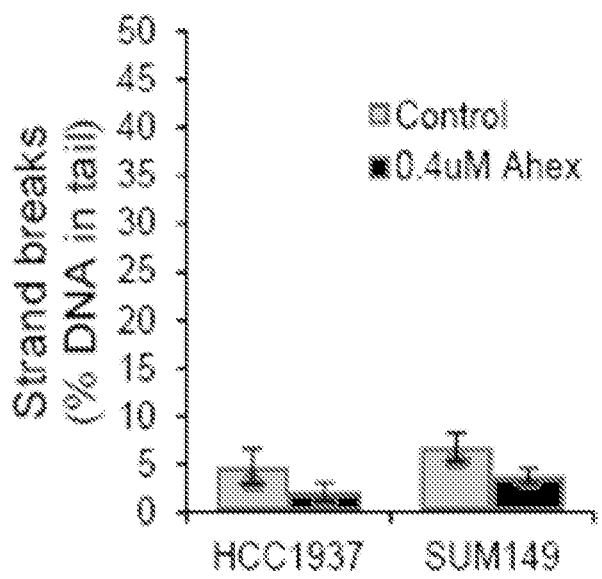

Given that DNA damage activates DNA repair mechanisms (Jackson et al., Nature 461, 1071-1078 (2009)), we tested whether or not acetohexamide induced DNA damage, and thereby indirectly activated DNA repair. Acetohexamide, in contrast to $H_2O_2$ (positive control), did not significantly induce DNA strand breaks compared to the vehicle control in both BER-defective and BER-proficient cells as displayed by the alkaline comet assay (FIG. 12A-12B and data not shown), which suggests that acetohexamide increases BER directly, rather than indirectly through induction of DNA damage. Perhaps the best example is activation of the tumor suppressor p53 via small molecules that inhibit mdm2, a negative regulator of p53. Alternatively, direct activation of BER may occur as evidence suggests that altering protein interactions or the acetylation state of APE1 endonuclease may stimulate BER activity (Fishel et al., Mol Aspects Med 28, 375-395 (2007)).

Example 10: Structure-Activity Relationship (SAR) Mini Analysis

To further validate the BER activity of acetohexamide, we conducted a SAR mini-analysis using analogs that included BA-4, BA-5, and BA-9, which were chosen based on minimal substitutions and commercial availability, and glipizide, which was identified as a hit in our screen but with lower significance than acetohexamide. Other acetohexamide analogs were present in the screened library but were not identified as hits (presumably due to multiple substitutions), and as a result were not included in this analysis.

Figure 13A:
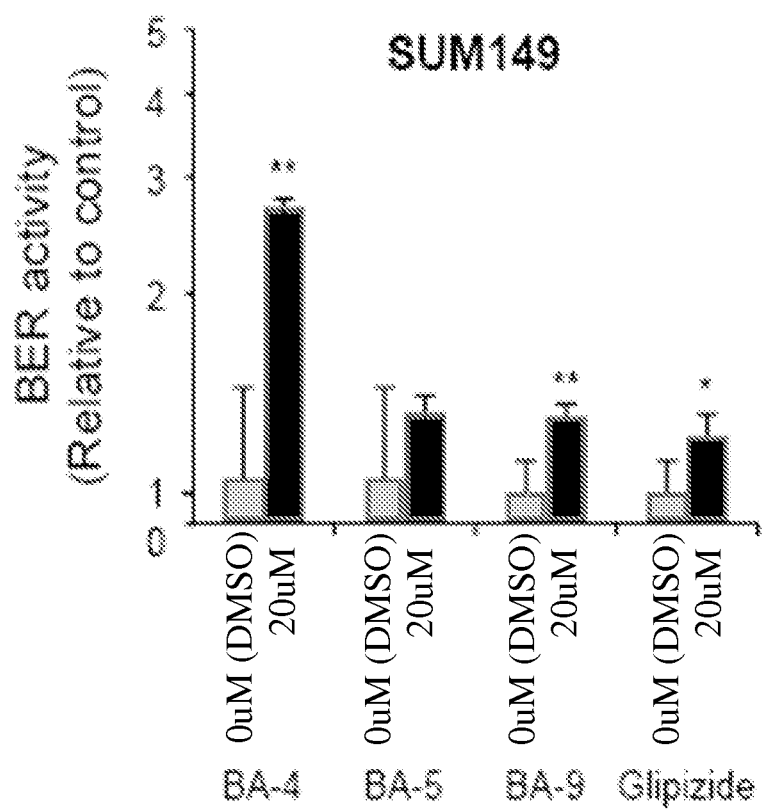
FIG. 13A, 13B is a pair of bar graphs showing the effect of acetohexamide analogs on BER activity in SUM149 (FIG. 13A) and MCF7 (FIG. 13B) cells. Unless otherwise indicated, all data are means and represent at least three independent experiments, error bars denote s.d., and p-values are relative to the control. *, p<0.05; **, p<0.01. Ahex=acetohexamide; 8oxoG=8-oxoguanine adducts; MMECs, mouse mammary epithelial cells.

BA-4, BA-9, and glipizide significantly increased BER compared to the vehicle control in SUM149PT cells (p=0.006, 0.01, 0.04, respectively; FIG. 13A). BA-5 also increased BER in these cells but without statistical significance (p=0.2; FIG. 13A). This observation may be due to instability of the BA-5 molecule; LC/MS analysis of BA-4, BA-5, and BA-9 revealed peaks consistent with the MW of each compound, but also revealed a degradation product associated with BA-5 (data not shown).

Figure 13B:
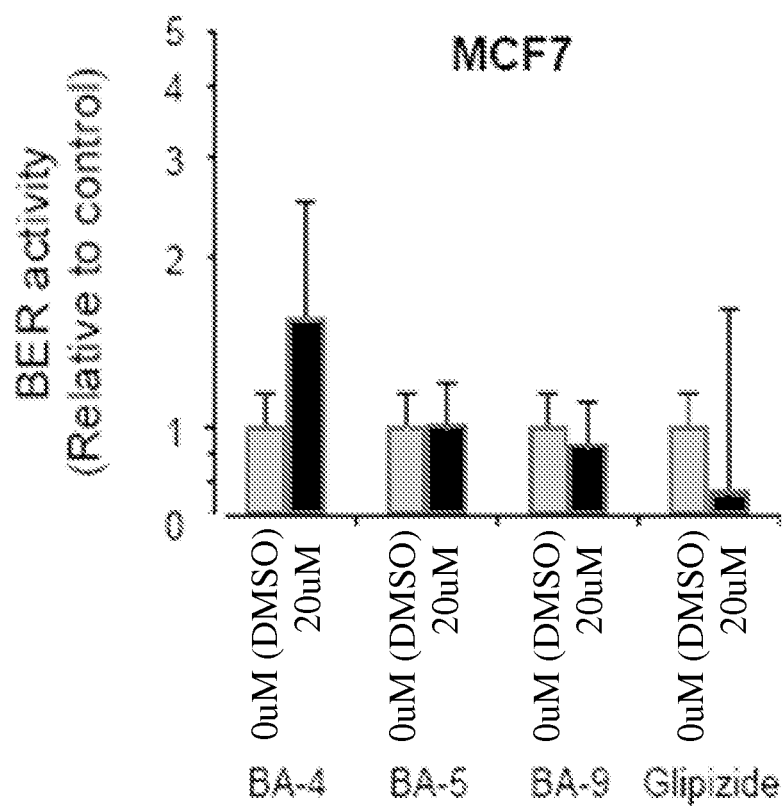

On the other hand, none of the four analogs significantly increased repair in BER-proficient MCF7 cells (BA-4, p=0.3; BA-5, p=0.5; BA-9, p=0.2; glipizide, p=0.2; FIG. 13B). Interestingly, the observed BER activity was consistent with that predicted by priority scoring as evidenced by the greater levels of relative BER activity of acetohexamide (1.68±0.13; summed priority score=7; FIG. 7A-7B) compared to glipizide (1.22±0.12; summed priority score=2; FIG. 13A-13B).

Overall, these SAR data support the selective activity of acetohexamide for enhancing repair of ODD in BER-defective cells.

Example 11: Analysis of Benserazide in Preventing BRCA1 Tumorigenesis

Figure 14A:
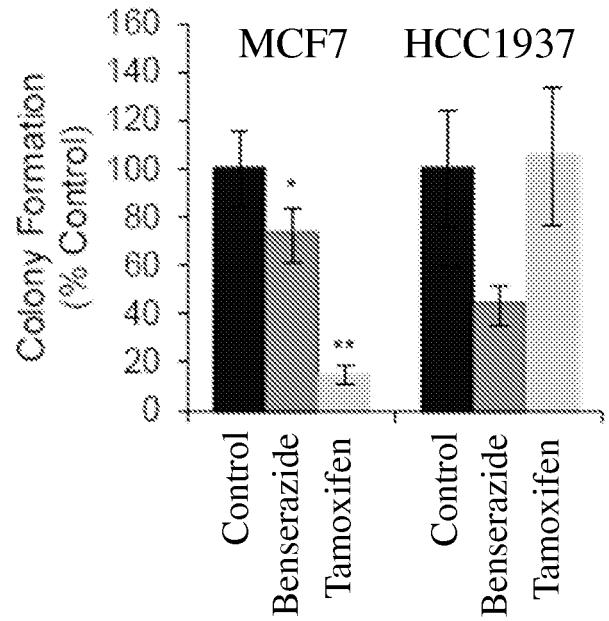
FIG. 14A, 14B is a pair of bar graphs showing benserazide prevented in vitro tumorigenesis in BRCA1-mutated/deficient cell lines.
Figure 14B:
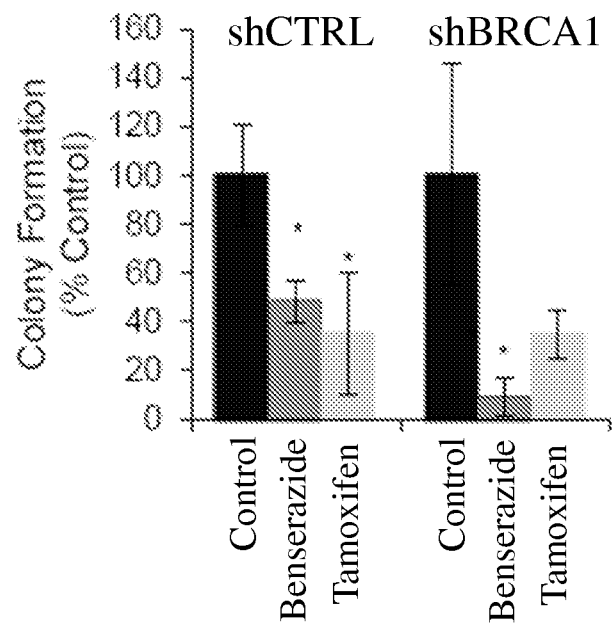

Benserazide was superior to tamoxifen at reducing in vitro tumorigenic potential of BRCA1-mutant/deficient cells. BRCA1 wild-type (MCF7) and mutant (HCC1937) cells (FIG. 14A) as well as MCF7 cells stably transduced with shRNA to BRCA1 or non-targeting control (FIG. 14B) were treated with vehicle control, 20 µM benserazide, or 1 µM tamoxifen and subjected to the soft agar colony formation assay, i.e. the standard assay for in vitro tumorigenesis. Colony formation represents tumorigenic potential. Tamoxifen is the current FDA-approved chemoprevention agent for breast cancer and a therapeutically-equivalent dose was used for comparison.

Figure 14C:
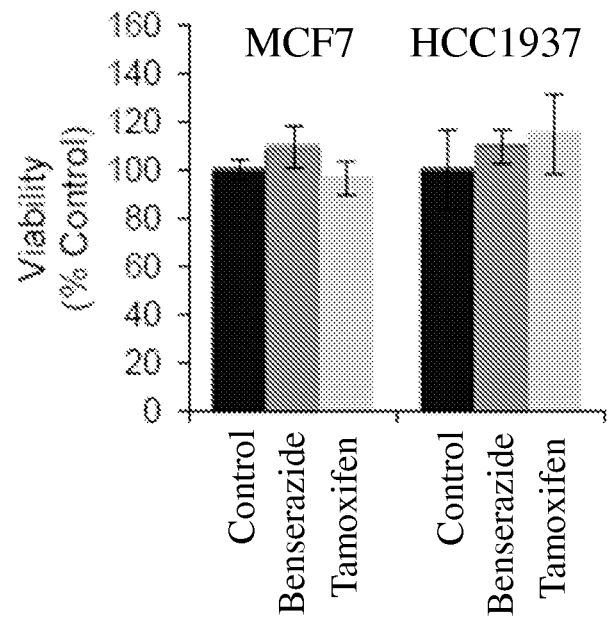
FIG. 14C is a bar graph showing benserazide-mediated reduction of in vitro tumorigenic potential was not due to a decrease in cell viability.

In FIG. 14C, BRCA1 wild-type (MCF7) and mutant (HCC1937) cells were simultaneously treated and then analyzed for cell viability by the trypan blue exclusion assay.

For in vivo tumorigenesis, we utilized a mouse xenograft model that began treatment with the DNA repair-activating agent 24 hours prior to inoculation of HCC1937 cells into the mammary fat pad. Treatment with vehicle control, 50 mg/kg benserazide, or 250 mg/kg benserazide continued daily for up to 60 days while monitoring for tumor formation by palpitation. After the 60 days (i.e. study endpoint), serum was collected for analysis of 8oxodG levels, tumors (if present) were excised and weighed, and anatomy was analyzed for metastasis. This model system feasibly allowed for completion of an in vivo study that mimicked chemoprevention conditions. Interestingly, benserazide increased the percentage of tumor-free mice in a dose-response manner and delayed tumor formation over time; it also acted in a dose response manner to increase serum levels of 8oxodG, a by-product of DNA repair, and decrease tumor weights at the study endpoint (data not shown). Furthermore, the average serum levels of 8oxodG negatively correlated with the average tumor weight among treatment groups (r=−0.82) (data not shown), suggesting that benserazide-mediated BER is proportional to the prevention of in vivo tumorigenesis. Finally, unlike the vehicle control, both concentrations of benserazide prevented metastasis (data not shown).

Example 12: Analysis of the Molecular Target of Benserazide

Benserazide and its analog, carbidopa, are both known to function as DOPA decarboxylase inhibitors. Carbidopa has the following structure:

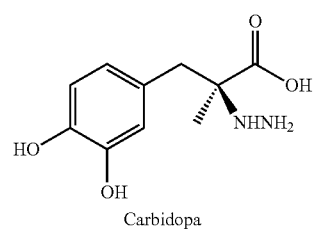 [SMILES: C[C@@](Cc1ccc(O)c(O)c1)(NN)C(=O)O]

Carbidopa

Benserazide and carbidopa were also both included among the compounds screened for BER-enhancing activity (FIG. 3A-3B). However, our screen did not identify carbidopa as a hit. Therefore, we first validated our screening data by subjecting the mutant BRCA1-containing SUM149 cell line to the BER assay following pre-treatment with vehicle control or carbidopa. Given that benserazide is typically administered at approximately half the dose of carbidopa (Greenacre et al., "Comparison of levodopa with carbidopa or benserazide in parkinsonism," Lancet 2:381-384 (1976)), we used carbidopa at the dose equivalent to the effective dose of benserazide (10 µM) and at the highest screened concentration or twice the effective dose of benserazide (20 µm). Indeed, carbidopa exhibited no effect on repair activity compared to the vehicle control (10 µM, p=0.4; 20 µM, p=0.3) (data not shown). We next asked whether carbidopa had an effect on in vitro tumorigenesis. The soft agar colony formation assay revealed that compared to the vehicle control, treatment with 10 µM or 20 µM carbidopa had no significant effect on colony formation of MCF7 cells transduced with either shRNA to BRCA1 (10 µM, p=0.09; 20 µM, p=0.1) or a non-targeting control (10 µM, p=0.7; 20 µM, p=0.4) (data not shown). Taken together, unlike benserazide, its carbidopa analog does not function as a DNA repair-activating agent or prevent tumorigenesis, suggesting that the benserazide-mediated effects on BER of ODD and tumorigenesis are independent of DOPA decarboxylase inhibition.

Example 13: Measuring DNA Damage to Identify a Candidate Subject

This example is taken from Collins et al. "Molecular Epidemiology and Cancer Prevention", Carcinogenesis, Vol. 24, No. 3, 511-515, March 2003.

DNA Damage Estimation with the Comet Assay

DNA breaks are measured using the comet assay (single cell gel electrophoresis). Immediately after isolation, lymphocytes are suspended in a 9:1 mixture of fetal calf serum and dimethylsulphoxide at 3×106/ml. Aliquots (100 µl) are slowly frozen to −80° C. and stored in liquid nitrogen. They are thawed, centrifuged and suspended in phosphate-buffered saline (PBS). Strand breaks are introduced in certain aliquots of lymphocyte by incubating them with 100 µM $H_2O_2$ in PBS for 5 min on ice. The cells are washed with PBS, centrifuged, suspended (at ~2×10$^5$ cells/ml) in 85 µl of 1% low melting point agarose (Life Technologies, Paisley, UK) at 37° C., and placed on a glass microscope slide (precoated with agarose to aid attachment of the gels). Two gels are prepared for each sample. The gels are allowed to set at 4° C., and cells are lysed for 1 h in 2.5 M NaCl, 0.1 M $Na_2EDTA$, 10 mM Tris-HCl, pH 10, 1% Triton X-100 at 4° C. Lysis removes membranes, cytoplasm and most nuclear proteins, leaving DNA as nucleoids.

To measure strand breaks, the slides are immersed in 0.3 M NaOH, 1 mM $Na_2EDTA$ for 40 min at 4° C. before electrophoresis at 0.8 V/cm for 30 min at an ambient temperature of 4° C. After neutralization, gels are stained with 4',6-diamidine-2'-phenylindole dihydrochloride, and viewed by fluorescence microscopy. Nucleoid DNA extends under electrophoresis to form 'comet tails', and the relative intensity of DNA in the tail reflects DNA break frequency. Tail intensity is assessed with a visual scoring method; 100 comets selected at random are graded according to degree of damage into five classes (0-4) to give an overall score for each gel of between 0 and 400 arbitrary units. The visual score correlates closely with the mean % of DNA in the tail and with the DNA break frequency. $H_2O_2$-induced strand breaks are estimated by subtracting comet scores of untreated cells from scores of cells treated with $H_2O_2$.

For analysis of endogenous base oxidation, after the lysis stage agarose-embedded nucleoids from non-$H_2O_2$-treated cells are incubated with endonuclease III (specific for oxidized pyrimidines) or with formamidopyrimidine DNA glycosylase (FPG; recognizes altered purines including 8-oxoGua) in 40 mM HEPES, 0.1 M KCl, 0.5 mM $Na_2EDTA$, 0.2 mg/ml bovine serum albumin, pH 8.0, or with this buffer alone, for 30 min at 37° C. Alkaline treatment and electrophoresis then followed. Net enzyme-sensitive sites, calculated by subtracting the comet score after incubation with buffer alone from the score with enzyme, indicate the extent of base oxidation. The enzymes are prepared as crude extracts from bacteria containing over-producing plasmid vectors, originally obtained from Dr R. Cunningham (State University of New York, USA; endonuclease III) and from Dr S. Boiteux (Institute Gustave-Roussy, Villejuif, France; FPG).

In Vitro Assay for DNA Repair

The modification of the comet assay to measure the base excision repair capacity of a cell extract has been described. It depends on the incubation of extract with substrate DNA comprising gel-embedded nucleoids from cells treated previously with a specific DNA-damaging agent.

Immediately after isolation, lymphocytes (5×10$^6$ in 50 µl aliquots), in 45 mM HEPES, 0.4 M KCl, 1 mM EDTA, 0.1 mM dithiothreitol, 10% glycerol, pH 7.8, are snap-frozen to −80° C. On thawing, lysis is completed by adding 12 µl of 1% Triton X-100, and the lysate is centrifuged. The supernatant is mixed with 4 volumes of 45 mM HEPES, 0.25 mM EDTA, 2% glycerol, 0.3 mg/ml bovine serum albumin, pH 7.8 (lymphocyte extract). Substrate nucleoids are prepared from HeLa cells (a human transformed endothelial cell line), treated on ice with the photosensitizer Ro 19-8022 (Hoffmann La Roche, Basel, Switzerland) at 0.2 µM plus visible light (4 min irradiation at 330 mm from a 1000 W tungsten halogen lamp) to induce 8-oxoGua. The cells are embedded in agarose and lysed as for the standard comet assay, and then incubated (in duplicate) with 40 µl of lymphocyte extract for 0 or 10 min at 37° C. Alkaline treatment and electrophoresis followed as in the standard comet assay. Incision rate is estimated as the increase in comet score from 0 to 10 min of incubation.

Semi-Quantitative PCR of OGG1 and APE1

RNA is extracted from lymphocytes using an Absolutely RNA kit (Stratagene, Amsterdam, The Netherlands). Total RNA is analysed with an Agilent Bioanalyser 2100 (Agilent Technologies, Stockport, UK) to confirm quality and quantity prior to Q-PCR. An aliquot (0.5 µg) is used for first strand cDNA synthesis at 42° C. using Superscript II reverse transcriptase (Life Technologies, Paisley, UK) according to the manufacturer's instructions. PCR is performed using 18S specific primers as an internal reference (94° C. for 1 min, 55° C. for 1 min, 72° C. for 1 min). Specific primer pairs for OGG1 are designed to amplify across intronic regions. Hot start PCR is performed using 10 pmol 18S primers and 50 pmol of OGG1 or APE1 primers, 2 U Taq (Promega, Southampton, UK) in the presence of 200 µM dNTPs and 1.5 mM $MgCl_2$. PCR products are verified by DNA sequencing and quantified at exponential phase of cycling using a DNA 500 chip (Agilent Technologies).

Example 14: Use of Family History to Identify a Candidate Subject

The following example is taken from an American Society of Clinical Oncology (ASCO) expert statement.

The gold standard family history is the comprehensive, three-generation pedigree used in medical genetics, counseling, and research settings (Wilson B J, Qureshi N, Santaguida P, et al. "Systematic review: family history in risk assessment for common diseases." Ann Intern Med 2009;

151:878-85). ASCO recommends the minimum adequate family history for cancer patients be defined as family history of cancer in first and second degree relatives. First degree relatives are parents, children, and full siblings. Second degree relatives are grandparents, aunts/uncles, nieces/nephews, grandchildren, and half siblings. For each relative with cancer, the following should be recorded:

Type of primary cancer(s)
Age at diagnosis of each primary cancer
Lineage (maternal and/or paternal)
Results of any cancer predisposition testing in any relative.

Red flags for hereditary cancer predisposition include early age of onset of cancer, multiple affected relatives with cancer on the same side of the family, and multiple primary tumors in a single individual. In addition emerging research suggests that individuals with specific tumor types should be considered for genetic testing regardless of family history. Individuals with these tumor types should be referred for genetic counseling and possible genetic testing regardless of family history. These include:

Triple negative (ER/PR/Her2neu negative) breast cancer, particularly if diagnosed under age 60
Epithelial ovarian cancer, fallopian tube cancer, or primary peritoneal cancer (most commonly, high grade serous histology)
Colorectal cancer demonstrating mismatch repair deficiency (via tumor studies including microsatellite instability analysis and/or immunohistochemistry, excluding known somatic causes including hypermethylation of MLH1 promoter and somatic BRAF mutation)
Endometrial cancer demonstrating mismatch repair deficiency (Via tumor studies including microsatellite instability analysis and/or immunohistochemistry, excluding known somatic causes including hypermethylation of MLH1 promoter)
Rare and/or pediatric tumors
  Medullary thyroid cancer
  Pheochromocytoma or paraganglioma
  Pediatric patients with adrenocortical carcinoma choroid plexus tumor, osteosarcoma or rhabdomyosarcoma.

Candidates with a family history suggestive of a predisposition for developing certain types of cancer should also, be provided with genetic testing, but such is not required for purposes of defining the present methods.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method of reducing the risk of cancer in a subject having a mutation in BRCA1, comprising administering to said subject an effective amount of a DNA repair agent which is benserazide.

2. The method of claim 1 further comprising a step wherein a DNA repair assay is conducted on a cell from the subject.

3. The method of claim 1 further comprising the step of testing said subject for the presence of a BRCA1 mutation by determining a genotype of a normal somatic cell from said subject.

4. The method of claim 3 further comprising the step of testing a somatic cell from said subject for a level of base excision repair activity.

5. The method of claim 4 wherein said testing comprises transfecting the somatic cell with an oxidatively damaged vector that is expressed only after repair of oxidative damage by the cell.

6. The method of claim 1, further comprising, prior to said administering, evaluating said subject by a base excision repair activity assay.

7. The method of claim 1, further comprising measuring a level of oxidative DNA damage in a sample from said subject selected from the group consisting of: a cell sample, a urine sample, a serum sample, and a saliva sample.

8. The method of claim 1 wherein the cancer is breast cancer or ovarian cancer.

9. The method of claim 1 wherein the cancer is breast cancer.

10. The method of claim 1, further comprising taking a family history from the subject.

11. The method of claim 10, comprising taking a family history of first degree relatives from the subject.

12. The method of claim 11, further comprising taking a family history of second degree relatives from the subject.

13. The method of claim 1, wherein said administering is by oral administration.

14. The method of claim 1, wherein said administering is by parenteral administration.

15. The method of claim 5, wherein the vector is oxidatively damaged by photodynamic treatment.

* * * * *